(12) United States Patent
Matsumoto et al.

(10) Patent No.: US 7,244,798 B2
(45) Date of Patent: *Jul. 17, 2007

(54) (METH) ACRYLIC COMPOUND HAVING AN OXETANYL GROUP AND LIQUID CRYSTAL FILM PRODUCED BY USING SAME

(75) Inventors: Takuya Matsumoto, Yokohama (JP); Hitoshi Mazaki, Yokohama (JP); Toru Nakamura, Yokohama (JP); Masaaki Kobayashi, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 211 days.

This patent is subject to a terminal disclaimer.

(21) Appl. No.: 10/672,946

(22) Filed: Sep. 26, 2003

(65) Prior Publication Data
US 2005/0101752 A1    May 12, 2005

(30) Foreign Application Priority Data
Oct. 1, 2002  (JP) ............................. 2002-289226
Oct. 1, 2002  (JP) ............................. 2002-289227

(51) Int. Cl.
*C08F 118/02* (2006.01)
*C08K 19/38* (2006.01)
*C08K 19/34* (2006.01)
*C08K 19/20* (2006.01)

(52) U.S. Cl. ..................... 526/319; 428/1.3; 428/1.1; 252/299.01; 252/299.61

(58) Field of Classification Search ................ 252/299, 252/299.01, 299.61; 526/319; 428/1.3, 428/1.1
See application file for complete search history.

(56) References Cited

U.S. PATENT DOCUMENTS

| | | | |
|---|---|---|---|
| 5,147,682 A | | 9/1992 | Takiguchi et al. |
| 5,188,760 A | * | 2/1993 | Hikmet et al. ......... 252/299.01 |
| 5,863,457 A | | 1/1999 | Hasebe et al. |
| 5,882,842 A | | 3/1999 | Akaki et al. |
| 6,015,848 A | * | 1/2000 | Ikushima et al. ............. 523/427 |
| 6,088,077 A | * | 7/2000 | De Wit et al. ............... 349/117 |
| 6,136,225 A | * | 10/2000 | Meyer et al. .......... 252/299.01 |
| 6,166,100 A | | 12/2000 | Hiwara et al. |
| 6,171,518 B1 | * | 1/2001 | Hikmet et al. ......... 252/299.01 |
| 6,262,147 B1 | | 7/2001 | Ikushima et al. |
| 6,284,898 B1 | * | 9/2001 | Moszner et al. ............. 549/214 |
| 6,319,557 B1 | | 11/2001 | Ikushima et al. |
| 6,322,892 B1 | | 11/2001 | Takami |
| 6,582,862 B1 | | 6/2003 | Nakamura et al. |
| 6,656,595 B2 | * | 12/2003 | Nakajima et al. ........... 428/413 |
| 6,660,344 B2 | * | 12/2003 | Lub ........................... 428/1.1 |
| 6,712,992 B2 | * | 3/2004 | Prechtl et al. ........... 252/299.6 |
| 6,828,030 B2 | | 12/2004 | Arimura et al. |
| 2003/0104144 A1 | * | 6/2003 | Hammond-Smith et al. ..... 428/1.21 |

FOREIGN PATENT DOCUMENTS

| | | | |
|---|---|---|---|
| JP | 03-009321 A | | 1/1991 |
| JP | 04-057017 A | | 2/1992 |
| JP | 05-333313 A | | 12/1993 |
| JP | 06-308462 | * | 11/1994 |
| JP | 06308462 A | * | 11/1994 |
| JP | 08-020641 | * | 1/1996 |
| JP | 08-021915 A | | 1/1996 |
| JP | 08020641 A | * | 1/1996 |
| JP | 08-301859 | * | 11/1996 |
| JP | 10-120640 A | | 5/1998 |
| JP | 11-106380 | * | 4/1999 |
| JP | 2000-319527 A | | 11/2000 |
| JP | 2002-250805 A | | 9/2002 |
| WO | WO 02/28985 A1 | | 4/2002 |

OTHER PUBLICATIONS

Richard J. Lewis Sr. "Hawley's Condensed Chemical Dictionary", 14th Edition, John Wile & Sons, Inc., NY 2001, p. 825.*
Lewis, *Hawley's Condensed Chemical Dictionary*, 14th Ed., John Wiley & Sons, Inc., New York (2001).

* cited by examiner

*Primary Examiner*—David W. Wu
*Assistant Examiner*—M. Bernshteyn
(74) *Attorney, Agent, or Firm*—Akin Gump Strauss Hauer & Feld LLP

(57) ABSTRACT

The present invention provides a novel compound which is suitable as the starting material of a side-chain type liquid crystalline polymeric substance having a reactive group which is excellent in reactivity upon fixation of the liquid crystal orientation structure. The novel compound is a (meth)acrylic compound having an oxetanyl group represented by the formula (1)

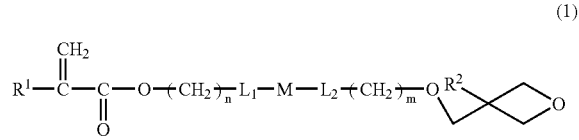

wherein $R^1$ is hydrogen or methyl, $R^2$ is hydrogen, methyl, or ethyl, "—$L_1$—M—$L_2$—" represents a mesogen portion, and n and m are each an integer of 0 to 10. The present invention also provides a liquid crystal film containing the side-chain type liquid crystalline polymeric substance and a liquid crystal display mounted with such a liquid crystal film.

12 Claims, 13 Drawing Sheets

(METH) ACRYLIC COMPOUND HAVING AN OXETANYL GROUP AND LIQUID CRYSTAL FILM PRODUCED BY USING SAME

BACKGROUND OF THE INVENTION

1. Field of the Invention

This invention relates to a novel (meth)acrylic compound having a polymerizable oxetanyl group and a novel side-chain type liquid crystalline polymeric substance derived from the (meth)acrylic compound. This invention also relates to a liquid crystal film containing such a polymeric substance and a liquid crystal display mounted with such a liquid crystal film.

2. Description of the Prior Art

In recent years, as a result of the researches and developments which have been actively conducted to apply liquid crystal materials to optical purposes, a liquid crystal film produced by aligning a liquid crystal material has practically used for the purposes of providing a liquid crystal display with color compensation and wide viewing angle properties.

Various methods of forming a liquid crystal material into a film are known. For example, there is a method in which a liquid crystal film is produced by forming a liquid crystalline polymeric substance film over a substrate which can align the substance and then heating the film to a temperature equal to or higher than the glass transition temperature "Tg", followed by rapid cooling of the film so as to fix the orientation of the liquid crystal, as disclosed in Japanese Patent Laid-Open Publication No. 3-9321. However, although this method is applicable to both main chain- and side chain-type liquid crystalline polymeric substances, it has problems that the process would be increased in load and eligible alignment substrates are limited when using a main-chain type liquid crystalline polymeric substance with a high Tg. Furthermore, when using a side-chain type liquid crystalline polymeric substance, this method has a problem in the heat resistance of the resulting liquid crystal film and a drawback that the orientation of the liquid crystal would be disordered at a temperature in the vicinity of the Tg.

Alternatively, as disclosed in Japanese Patent Laid-Open Publication, No. 8-21915, there is a method in which a liquid crystal film is produced by pouring a liquid crystalline low molecular weight substance having a reactive group into a liquid crystal cell provided with an alignment substrate and heating the cell to a temperature at which the substance exhibits a liquid crystal phase so as to be oriented in a liquid crystal orientation state, followed by fixing the orientation by polymerizing the substance with an external force such as light or heat. However, in this method, it is difficult to control the parameters of the resulting liquid crystal film because the liquid crystal to be oriented is a low molecular weight substance and thus the physical properties such as fluidity and birefringence are heavily dependent on temperature. Further, this method may often have a problem with the heat resistance of the resulting liquid crystalline film because the structure of the liquid crystal after polymerization becomes similar to that of a side chain-type liquid crystalline polymeric substance and thus the sufficiently high Tg can not be obtained.

As an alternative for polymerizing and fixing a liquid crystal orientation by an external force, there is a method in which a mixture of a liquid crystalline polymeric substance and a reactive low molecular weight substance is allowed to be oriented to a liquid crystal phase and subjected to an external force so as to be reacted and cured, as reported in Japanese Patent Laid-Open Publication No. 10-120640. However, because the reaction between the liquid crystalline polymeric substance and the reactive low molecular weight substance does not progress sufficiently, the Tg is not sufficiently raised, leading to a problem with the heat resistance of the resulting liquid crystal film.

In view of these problems, a method as disclosed in Japanese Patent Laid-Open Publication No. 2000-319527 is now considered to be the most effective in which method a reactive group is directly introduced into a liquid crystalline polymeric substance with a relatively low Tg, such as a side chain-type and then subjected to an external force such as light or heat to be cross-linked after orienting the reactive group to a liquid crystal state, thereby raising the Tg. However, this method has a problem that it is difficult to synthesize such a side chain-type liquid crystalline polymeric substance with a reactive group. For example, when the polymeric structure is constructed prior to the introduction of a reactive group, the amount thereof may be insufficient. On the other hand, in a method in which from a monomer having two reactive groups, a side chain-type liquid crystalline polymeric substance having a reactive group is synthesized by polymerizing one of the reactive group, it is necessary that the reactivity of the other reactive group must be maintained lower than that of the reactive group to be reacted, leading to a problem that the reactive group of the polymeric substance after being oriented to a liquid crystal phase tends to be insufficient.

The present invention was made in view of the foregoing problems and provides a novel compound which is suitable as the starting material of a side chain-type liquid crystalline polymeric substance having a reactive group with an excellent reactivity upon fixation of a liquid crystal orientation and a side chain-type liquid crystalline polymeric substance derived from such a compound. Furthermore, the present invention also provides a liquid crystal film with an excellent heat resistance which is produced from a liquid crystal material containing such a side chain-type liquid crystalline polymeric substance by fixing the orientation state of the liquid crystal material and a liquid crystal display mounted with the liquid crystal film.

After an extensive research and study made by the present inventors, they found a novel polymerizable compound having an oxetanyl group which can be used as the starting material of a side chain-type liquid crystalline polymeric substance which can be easily synthesized and is excellent in orientability and fixation of the orientation structure.

SUMMARY OF THE INVENTION

That is, according to a first aspect of the present invention, there is provided a (meth)acrylic compound having an oxetanyl group represented by the formula

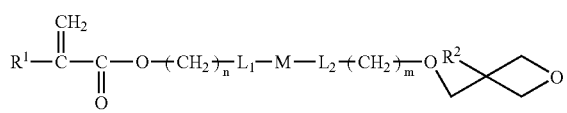

(1)

wherein $R^1$ is hydrogen or methyl, $R^2$ is hydrogen, methyl, or ethyl, $L_1$ and $L_2$ each are selected from a single bond, —O—, —O—CO—, and —CO—O—, M represents a formula selected from formulas (2), (3) and (4) below, and n and m are each independently an integer from 0 to 10:

—P₁—L₃—P₂—L₄—P₃— (2)

—P₁—L₃—P₃— (3)

—P₃— (4)

wherein P₁ and P₂ are each independently a group selected from formulas (5) below, P₃ is a group selected from formulas (6) below, and L₃ and L₄ are each independently selected from a single bond, —CH=CH—, —C≡C—, —O—, —O—CO— and —CO—O—:

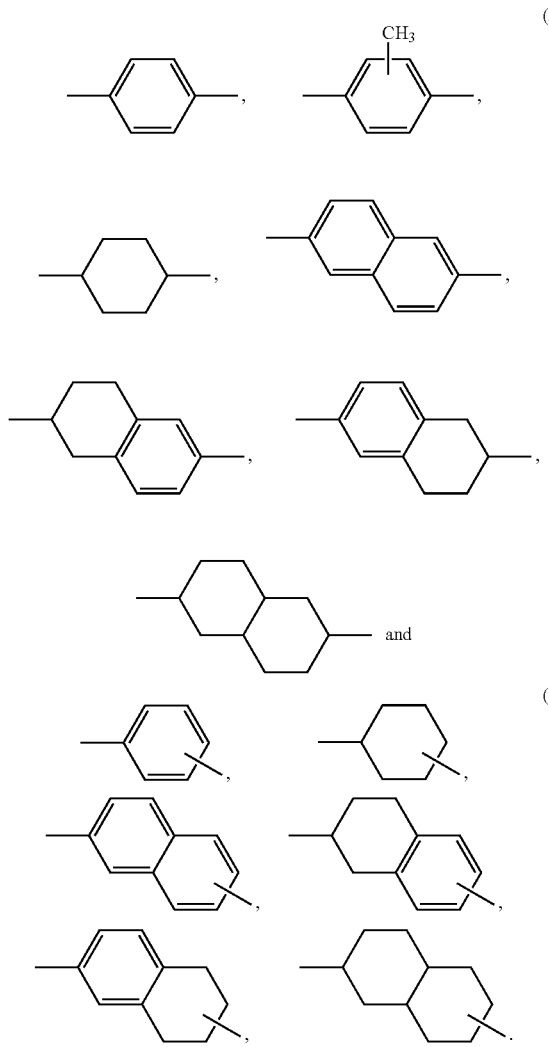

(5)

(6)

According to a second aspect of the present invention, there is provided a side chain-type liquid crystalline polymeric substance obtained by homopolymerizing the (meth) acrylic portion of the (meth)acrylic compound having an oxetanyl group represented by formula (1) or copolymerizing same with another (meth)acrylic compound.

According to a third aspect of the present invention, there is provided the side chain-type liquid crystalline polymeric substance having a unit represented by formula (7) below derived from a (meth)acrylic compound having an oxetanyl group of formula (1) above:

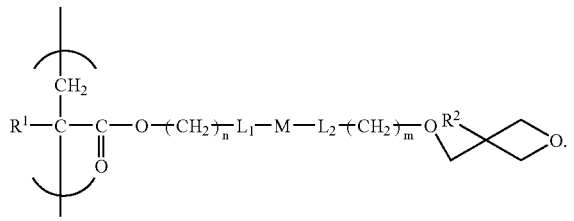

(7)

According to a fourth aspect of the present invention, there is provided the side chain-type liquid crystalline polymeric substance containing a unit of formula (7) above in an amount of 5 to 100 percent by mol.

According to a fifth aspect of the present invention, there is provided the side chain-type liquid crystalline polymeric substance of whose weight-average molecular weight is from 2,000 to 100,000.

According to a sixth aspect of the present invention, there is provided a liquid crystal material containing the side-chain type liquid crystalline polymeric substance in an amount of 10 percent by mass or more.

According to a seventh aspect of the present invention, there is provided the liquid crystal material which further contains a photo cationic initiator and/or a thermal cationic initiator.

According to an eighth aspect of the present invention, there is provided a liquid crystal film formed by fixing the orientation state of the liquid crystal material.

According to a ninth aspect of the present invention, there is provided a method of producing a liquid crystal film wherein the liquid crystal material is developed over an alignment substrate so as to align the liquid crystal material in a liquid crystal orientation state, followed by fixing the orientation by light irradiation and/or a heat treatment.

According to a tenth aspect of the present invention, there is provided the method of producing a liquid crystal film wherein the orientation state is one obtained by fixing a orientation state selected from the group consisting of nematic, twisted nematic, cholesteric, and nematic hybrid orientations.

According to an eleventh aspect of the present invention, there is provided an optical film comprising the liquid crystal film.

According to a twelfth aspect, there is provided the optical film is one selected from the group consisting of a retardation film, a color compensation film, a viewing angle improving film, a circular polarizing film, and an optical rotatory film.

DETAILED DESCRIPTION OF THE INVENTION

Figure 1:
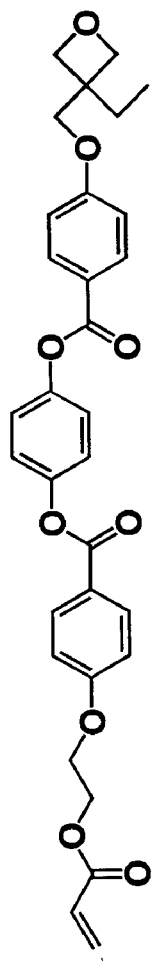
FIG. 1 shows the ¹H-NMR spectrum of the acrylic compound 1 obtained in Example 1.
Figure 1:
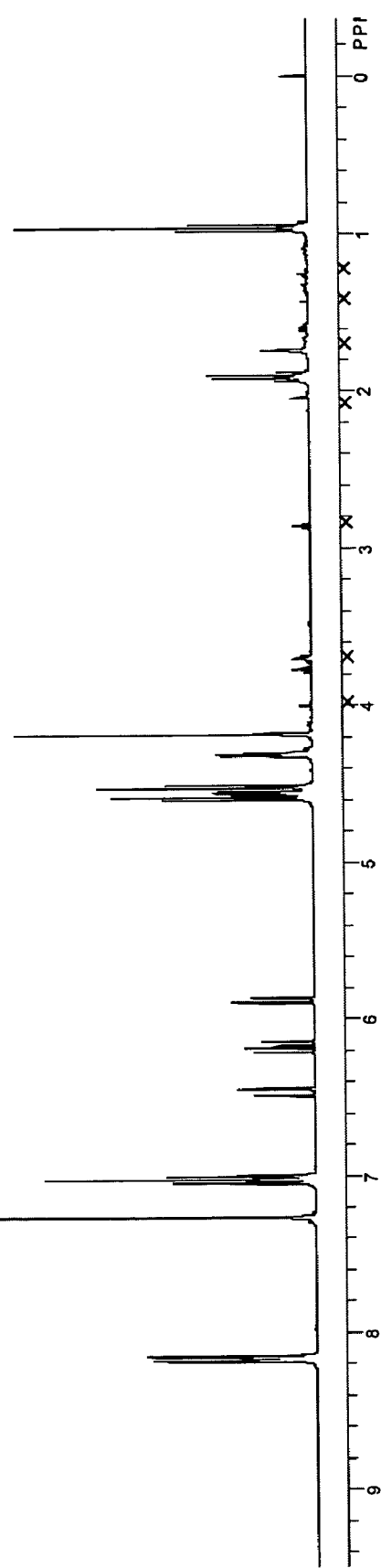

The present invention will be described in more detail below.

The (meth)acrylic compound having an oxetanyl group of the present invention is represented by the formula

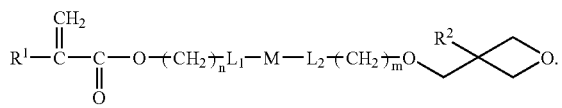

(1)

In formula (1), $R^1$ is hydrogen or methyl, $R^2$ is hydrogen, methyl, or ethyl, $L_1$ and $L_2$ each are selected from a single bond, —O—, —O—CO—, and —CO—O—, M represents a formula selected from formulas (2), (3) and (4) below, and n and m are each independently an integer from 0 to 10:

  (2)

  (3)

  (4)

wherein $P_1$ and $P_2$ are each independently a group selected from formulas (5) below, $P_3$ is a group selected from formulas (6) below, and $L_3$ and $L_4$ are each independently selected from a single bond, —CH═CH—, —C≡C—, —O—, —O—CO— and —CO—O—:

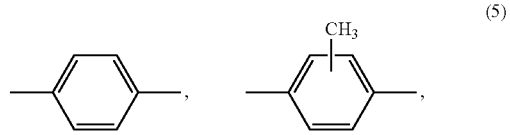  (5)

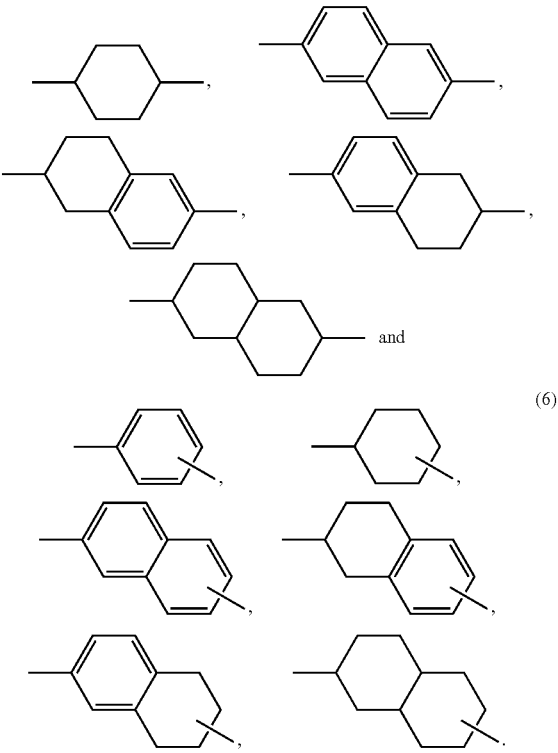

That is, the (meth)acrylic compound having an oxetanyl group of the present invention is characterized in that it contains a mesogen portion comprising an aromatic ester, spacer portions bonding thereto and comprising a hydrocarbon chain, a reactive oxetanyl group at one terminal end, and a (meth)acrylic group at the other terminal end as constituting units and a polymeric substance obtained by homopolymerizing the (meth)acrylic group of this compound or copolymerizing same with another (meth)acrylic compound exhibits liquid crystallinity.

First of all, each of the constituting units will be described.

The mesogen portion of the (meth)acrylic compound having an oxetanyl group of the present invention is represented by "—$L_1$—M—$L_2$—" in formula (1) wherein M is represented by "—$P_1$—$L_3$—$P_2$—$L_4$—$P_3$—", "—$P_1$—$L_3$—$P_3$—", or "—$P_3$—". The mesogen portion has such a structure that 1 to 3 aromatic- or cyclohexane-rings are bonded directly (single bond) or via an ether bond (—O—) or an ester bond (—CO—O—) to the spacer portion, oxetanyl group or (meth)acrylic group.

In formula (1), $L_1$, $L_2$, $L_3$, and $L_4$ are each independently a single bond (this means that the groups of the both sides bond directly without via the group represented by "L") or represents —CH═CH—, —C≡C—, —O—, —O—CO— or —CO—O—. $P_1$ and $P_2$ are each independently a group selected from formulas (5), while $P_3$ is a group selected from formulas (6).

Although the mesogen portion may be selected arbitrary from the above-described combinations, preferred examples are those represented by the following formulas:

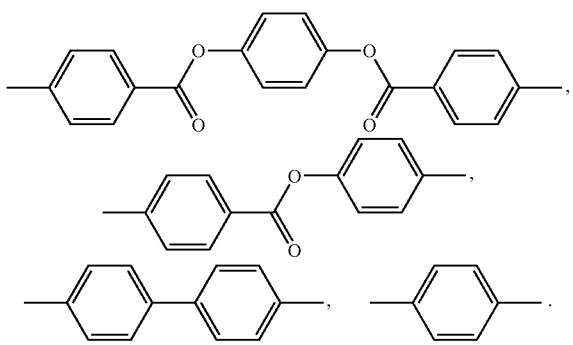

The spacer portions represented by "—(CH$_2$)$_n$—" and "—(CH$_2$)$_m$—" in formula (1) each represent a single bond which means that "n" or "m" is 0 or a divalent straight-chain hydrocarbon having 1 to 10 carbon atoms, i.e., "n" or "m" is an integer of 1 to 10. As long as the intended compound exhibits liquid crystallinity, the mesogen portion may bond directly without via the spacer portions or bond via an ether bond (—O—) or an ester bond (—CO—O—), to the oxetanyl group portion and the (meth)acrylic portion. In general, too short spacers between the mesogen portion and the (meth)acrylic group portion would narrow the temperature range at which the liquid crystallinity is exhibited, while too long spacers would adversely affect the heat resistance of the resulting liquid crystal film. In view of these, the spacer portions between the mesogen portion and the (meth)acrylic group portion has usually 1 to 8, preferably 2 to 6 carbon atoms. Too long spacers between the mesogen portion and the oxetanyl group portion would adversely affect the heat resistance of the resulting liquid crystal film. Therefore, the spacer portions between the mesogen portion and the oxetanyl group portion have usually 0 to 6, preferably 0 to 4 carbon atoms (0 carbon atoms denotes herein that the mesogen portion bonds directly to the oxetanyl group portion).

One of the terminal ends of the (meth)acrylic compound having an oxetanyl group of the present invention is a reactive oxetanyl group, while the other terminal end is a (meth)acrylic group. Since the compound is a difunctional monomer having both an oxetanyl group which is a cationic polymerizable group and a (meth)acrylic group which is radical- or anionic-polymerizable group, the (meth)acrylic group can be polymerized only by radical- or anionic-polymerization, thereby obtaining a side chain type-liquid crystalline polymeric substance having an oxetanyl group which is a cationic polymerizable group. That is, a side chain-type liquid crystalline polymeric substance is synthesized by anionic- or radical-polymerization of the (meth) acrylic group in the presence of the cationic polymerizable oxetanyl group whose reactivity is low under the conditions except those for cationic polymerization. A side chain-type liquid crystalline polymeric substance is lower in Tg than a main chain-type liquid crystalline polymeric substance and thus can be easily oriented at a low temperature. After orienting the side-chain type liquid crystalline polymeric substance thus obtained, the oxetanyl group is polymerized, i.e., cured and cross-linked in the presence of cations, resulting in the rise of Tg. Therefore, a liquid crystal film with improved heat resistance and mechanical strength can be produced from the resulting side chain-type liquid crystalline polymeric substance.

No particular limitation is imposed on the method of synthesizing the (meth)acrylic compound having an oxetanyl group which can, therefore, be synthesized using any of conventional organic chemistry synthesis methods.

For example, a portion having an oxetanyl group is coupled to a portion having a (meth)acrylic group by means of the Williamson's ether synthesis or an ester synthesis using a condensing agent thereby synthesizing a (meth)acrylic compound having two reactive functional groups, i.e., an oxetanyl group and a (meth)acrylic group. More specifically, the (meth)acrylic compound having an oxetanyl group of the present invention can be synthesized by the following processes:

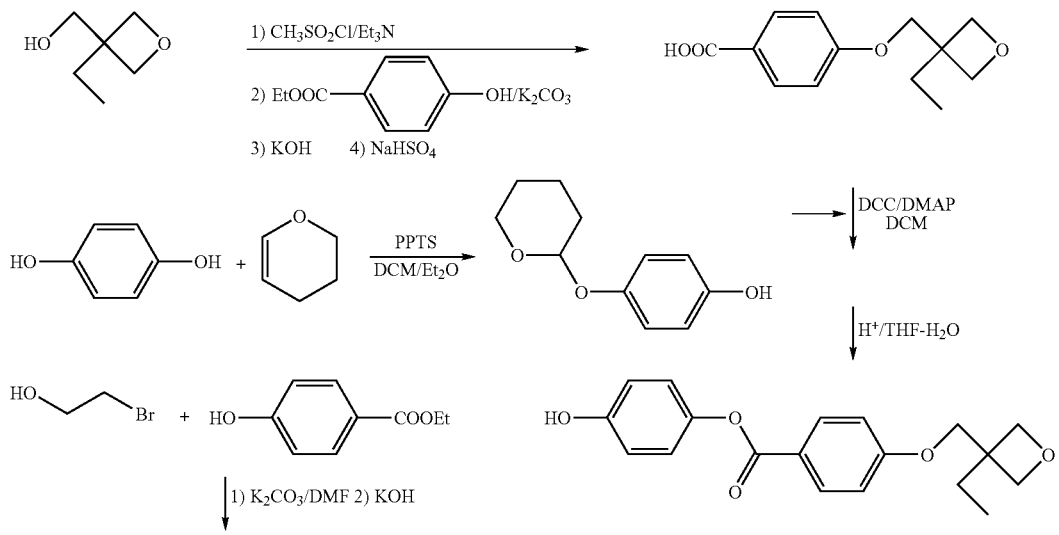

-continued

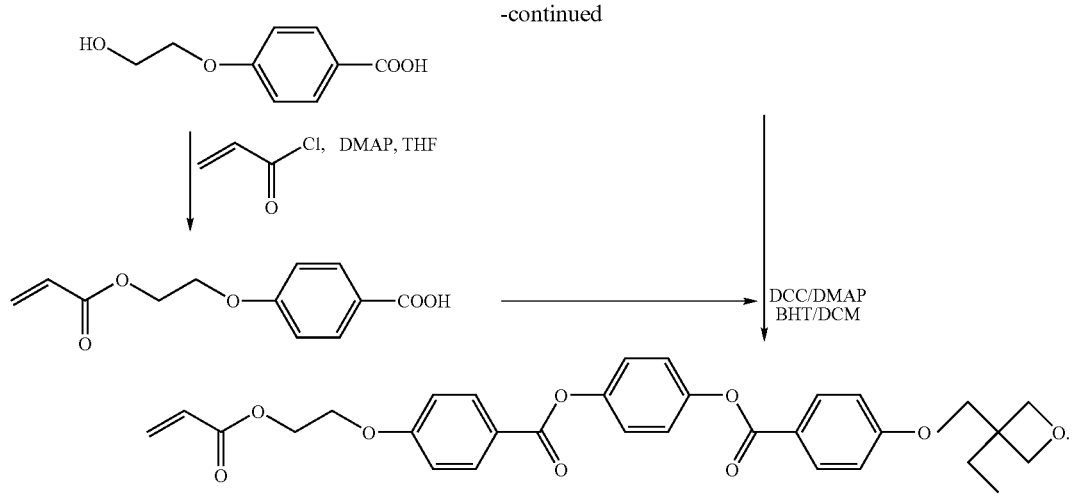

The abbreviations in the above formulas indicate the following compounds:
DCC: 1,3-dicyclohexylcarbodiimide
DMAP: 4-dimethylaminopyridine
DCM: dichloromethane
PPTS: pyridinium-p-toluene sulfonate
THF: tetrahydrofuran
DMF: dimethylformamide
BHT: 2,6-di-t-butyl-4-methylphenol The side chain-type liquid crystalline polymeric substance of the present invention is one containing a unit represented by formula (7) below derived from a (meth)acrylic compound having an oxetanyl group represented by formula (1):

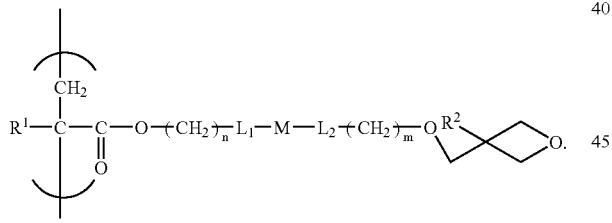

(7)

The side chain-type liquid crystalline polymeric substance containing a unit represented by formula (7) can be easily synthesized by homopolymerizing the (meth)acrylic group portion of the (meth)acrylic compound having an oxetanyl group of formula (1) or copolymerizing the same with another (meth)acrylic compound by way of radical or anionic polymerization. No particular limitation is imposed on the polymerization conditions. Therefore, the polymerization may be carried out under normal conditions.

As an example of the radical polymerization, a method may be used in which a (meth)acrylic compound is solved in a solvent such as dimethylformamide (DMF) and reacted at a temperature of 80 to 90° C. for several hours using 2,2'-azobisisobutylonitrile (AIBN) or benzoyl peroxide (BPO) as an initiator. Alternatively, a method is effective in which in order to allow the liquid crystal phase to be stably exhibited, a living radical polymerization is conducted using a copper (I) bromide/2,2'-bipyridyl-based or TEMPO-based initiator so as to control the molecular weight distribution. These radical polymerizations are needed to be conducted strictly under deoxidation conditions.

As an example of the anionic polymerization, a method may be used in which a (meth)acrylic compound is solved in a solvent such as tetrahydrofuran (THF) and reacted using a strong base such as organic lithium compounds, organic sodium compounds or a Grignard reagent. Alternatively, this polymerization can be converted to a living anionic polymerization by optimizing the initiator or reaction temperature thereby controlling the molecular weight distribution. These anionic polymerizations are needed to be conducted strictly under dehydration and deoxidation conditions.

No particular limitation is imposed on the type of a (meth)acrylic compound to be copolymerized as long as the compound exhibits a liquid crystallinity. However, preferred are (meth)acrylic compounds having a mesogen group because it can enhance the liquid crystallinity of the resulting polymeric substance. More specifically, particularly preferred are those as represented by the following formulas:

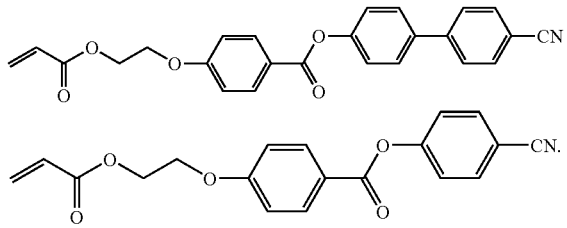

The side chain-type liquid crystalline polymeric substance of the present invention contains a unit of formula (7) in an amount of preferably 5 to 100 percent by mol and particularly preferably 10 to 100 percent by mol. The side chain-type liquid crystalline polymeric substance of the present invention has a weight average molecular weight of preferably 2,000 to 100,000 and particularly preferably 5,000 to 50,000.

Next, the polymeric liquid crystal material containing the side chain-type liquid crystalline polymeric substance of the present invention will be described herein below.

The polymeric liquid crystal material of the present invention contains the side chain-type liquid crystalline polymeric substance of the present invention in an amount of at least 10 percent by mass or more, preferably 30 percent by mass or more, and more preferably 50 percent by mass or more. A composition containing less than 10 percent by mass of the side chain-type liquid crystalline polymeric substance is not preferred because the concentration of the polymeric group in the composition will be reduced and thus the mechanical strength after the polymerization will be insufficient.

The polymeric liquid crystalline composition of the present invention may contain various compounds which can be mixed without disturbing the liquid crystallinity, other than the side chain-type liquid crystalline polymeric substance. Examples of such compounds are compounds having cationic polymerizable functional group such as oxetanyl, epoxy and vinylether groups, various polymeric substances having a film forming capability, and various low molecular- or polymeric-compounds exhibiting a nematic-, cholesteric-, or discotic liquid crystallinity. Furthermore, various optically active substances regardless of whether it exhibits a liquid crystallinity or not may be blended so as to allow the polymeric liquid crystalline composition to exhibit a cholesteric liquid crystallinity.

After the polymeric liquid crystal material of the present invention is subjected to an orientation treatment, the oxetanyl group is cross-linked by cationic polymerization thereby improving the heat resistance of the resulting liquid crystal film. Therefore, in order to allow the cationic polymerization to progress easily and rapidly, the polymeric liquid crystalline composition preferably contains a photo- or thermal-cation generator which generates cations by an external force such as light or heat. If necessary, various sensitizers may be used in combination.

The term "photo cation generator" used herein denotes a compound which can generate cations by irradiation of a light with a specific wavelength and may be organic sulfonium salt-, iodonium salt-, or phosphonium salt-based compounds. Counter ions of these compounds are preferably antimonate, phosphate, and borate. Specific examples are $Ar_3S^+SbF_6^-$, $Ar_3P^+BF_4^-$, and $Ar_2I^+PF_6^-$ wherein Ar indicates a phenyl or substituted phenyl group. Sulfonic acid esters, triazines, diazomethanes, β-ketosulfone, iminosulfonato, and benzoinsulfonate are also eligible.

The term "thermal cation generator" used herein denotes a compound which can generate cations by being heated to a certain temperature and may be benzylsulfonium salts, benzylammonium salts, benzylpyridinium salts, benzylphosphonium salts, hydradinium salts, carbonic acid esters, sulfonic acid esters, amineimides, antimony pentachloride-acetyl chloride complexes, diaryliodonium salt-dibenzyloxy copper, and halogenated boron-tertiary amine adducts.

Since the amount of the cation generators to be added in the polymeric liquid crystalline composition varies depending on the structure of the mesogen portion or spacer portions constituting the side chain-type liquid crystalline polymeric substance to be used, the equivalent weight of the oxetanyl group, and the conditions for liquid crystal orientation, it can not be determined with certainty. However, it is within the range of usually 100 ppm by mass to 20 percent by mass, preferably 100 ppm by mass to 10 percent by mass, more preferably 0.2 percent by mass to 7 percent by mass, and most preferably 0.5 percent by mass to 5 percent by mass. The amount of less than 100 ppm by mass is not preferred because the polymerization may not progress due to the insufficient amount of cation to be generated. The amount of more than 20 percent by mass is not also preferred because the cation generator remains in a large amount in the resulting liquid crystal film and thus the light resistance thereof would be deteriorated.

Next, the method of producing a liquid crystal film using a liquid crystal material containing the above-described polymeric liquid crystalline composition will be described hereinafter. Although not restricted, the liquid crystal film may be produced by developing the liquid crystal material over an alignment substrate to be oriented and fixing the orientation by subjecting the material to light irradiation and/or a heat treatment.

First of all, the liquid crystalline material of the present invention is developed over an alignment substrate thereby aligning the material. Examples of the alignment substrate are films of such as polyimide, polyphenylene sulfide, polyphenylene oxide, polyether ether ketone, polyethylene naphthalate, polyethylene terephthalate, polyarylate, and triacetyl cellulose. Although some of these films exhibit a sufficient capability to align the liquid crystalline material and thus can be used as aligning substrates as they are, most of them are used after being subjected to a treatment such as rubbing, stretching, polarization irradiation, or skew ray irradiation such that the films exhibit or are enhanced in alignment capability. Alternatively, a conventional alignment film such as polyimide, polyvinyl ether, or polyvinyl cinnamate may be laminated over the substrate film and subjected to a treatment such as rubbing, stretching, polarization irradiation, or skew ray irradiation so as to impart the aligning capability.

In the case where there are problems that the alignment substrate to be used is not optically isotropic, the resulting liquid crystal film is opaque at a wavelength region where it is intended to be used, or the alignment substrate is so thick that it causes a problem in practical use, the alignment substrate may be used temporarily until the liquid crystal film is laminated over and transferred to an optically isotropic film or a transparent film with which the liquid crystal film is transparent at a wavelength region where it is intended to be used or attached to a liquid crystal cell. The transferring method may be any conventional method. For example, as disclosed in Japanese Patent Laid-Open Publication Nos. 4-57017 and 5-333313, there may be used a method in which after a liquid crystal layer with an alignment substrate is laminated via a pressure sensitive adhesive or adhesive over a substrate on which the liquid crystal layer is to be transferred and the surface is cured using an pressure-sensitive adhesive or adhesive, only the liquid crystal film is transferred on the substrate by peeling off the alignment substrate.

Examples of the substrate onto which the liquid crystal layer is transferred are a triacetyl cellulose film such as Fujitack (manufactured by Fuji Photo Film Co., Ltd.) and Konicatack (manufactured by Konica Corp.); a transparent film such as TPX film (manufactured by Mitsui Chemical Inc.), Arton film (manufactured by JSR), Zeonex film (manufactured by Nippon Zeon Co., Ltd) and Acryprene film (manufactured by Mitsubishi Rayon Co., Ltd.); and a polyethylene terephthalate film treated with silicone or provide on its surface with a peelable layer. If necessary, the liquid crystal film may be transferred directly to a polarizing film.

No particular limitation is imposed on the pressure sensitive adhesive or adhesive to be used for transferring the liquid crystal film as long as it is of optical grade. Therefore, there may be used conventional acrylic-, epoxy-, or urethane-based ones.

The liquid crystal material is developed on an alignment substrate and formed into a liquid crystal material layer by a method in which the liquid crystal material in a molten state is coated directly over an alignment substrate or a method in which a solution of the liquid crystal material is coated over an alignment substrate and dried to remove the solvent.

No particular limitation is imposed on the solvent used for preparing the solution as long as it can dissolve the liquid crystal material of the present invention and be evaporated under appropriate conditions. Preferred examples of the solvent are ketones such as acetone, methyl ethyl ketone, and isophorone; ether alcohols such as butoxyethyl alcohol, hexyloxyethyl alcohol, and methoxy-2-propanol; glycol ethers such as ethylene glycol dimethyl ether and diethylene glycol dimethyl ether; esters such as ethyl acetate and ethyl lactate; phenols such as phenol and chlorophenol; amides such as N,N-dimethylformamide, N,N-dimethylacetoamide, and N-methylpyrrolidone; halogen-based solvents such as chloroform, tetrachloroethane, and dichlorobenzene; and mixtures thereof. A surfactant, a defoaming agent, or a leveling agent may be added to the solution so as to form a uniform film layer on an alignment substrate.

No particular limitation is imposed on the methods of coating the liquid crystalline material directly or the solution thereof as long as they can ensure the uniformity of the film layer. Therefore, there may be used any conventional method. Examples of the method are spin coating, die coating, curtain coating, dip coating, and roll coating methods.

In the method of coating the liquid crystal material solution, it is preferred to add a drying process for removing the solvent after coating. No particular limitation is imposed on the drying method as long as it can maintain the uniformity of the film layer. Therefore, there may be used any conventional method and thus the solvent may be removed in a heater (furnace) or blowing hot air.

The liquid crystal material layer formed on an alignment substrate is subjected to a heat treatment or the like so as to form a liquid crystal orientation and further subjected to light irradiation and/or a heat treatment to fix the orientation. In the first heat treatment, the liquid crystal material is heated to a temperature at which it exhibits a liquid crystal phase so as to allow the material to be oriented with a self-orientability which the material naturally has. Since the conditions for the heat treatment vary in the optimum conditions and limits depending on the liquid crystal phase behavior temperature (transition temperature) of the liquid crystal material to be used, it can not be determined with certainty. However, it is within the range of usually 10 to 250° C. and preferably 30 to 160° C. The liquid crystal material layer is heated at preferably a temperature equal to the glass transition temperature or higher and more preferably a temperature which is 10° C. higher than the glass transition temperature. A too low temperature is not preferred because there is a possibility that the orientation to the liquid crystal phase does not progress sufficiently, while a too high temperature is not also preferred because the cationic polymerizable reactive group in the liquid crystal material and the alignment substrate are adversely affected. The heat treatment is conducted for usually 3 seconds to 30 minutes and preferably 10 seconds to 10 minutes. The heat treatment for less than 3 seconds is not preferred, because there is a possibility that the orientation may not be achieved sufficiently. Whereas the heat treatment for longer than 30 minutes is not also preferred, because the productivity is deteriorated.

After forming the liquid crystal orientation by subjecting the liquid crystal material layer to the heat treatment or the like, the liquid crystal material is cured with the polymerization reaction of the cationic polymerizable reactive group in the composition while maintaining the liquid crystal orientation state. This curing process is conducted to fix the liquid crystal orientation thus formed by a curing (cross-linking) reaction thereby modifying the film layer to be harder.

As described above, since the liquid crystal material of the present invention has a cationic polymerizable reactive group, it is preferred to use a cationic polymerization initiator (cation generator) for polymerizing (cross-linking) the reactive group. As such a polymerization initiator, a photo cation generator is preferred to a thermal cation generator.

In the case of using a photo cation generator, after addition thereof, the processes prior the thermal treatment for the liquid crystal orientation are conducted under dark conditions (conditions where light is shielded to an extent that the photo cation generator does not dissociate) whereby the liquid crystalline material does not cure until being subjected to the orientation process and thus can be oriented to a liquid crystal phase while maintaining sufficient flowability. Thereafter, a light from a light source capable of emitting an appropriate wavelength of light is irradiated so as to generate cations thereby curing the liquid crystal material.

The light irradiation is conducted by irradiating a light from a light source having a spectrum in an absorption wavelength of the photo cation generator to be used such as a metal halide lamp, a high-pressure mercury lamp, a low-pressure mercury lamp, a xenon lamp, an arc discharge lamp, and a laser thereby decomposing the photo cation generator. The irradiation dose per $cm^2$ is within the range of generally 1 to 2000 mJ and preferably 10 to 1000 mJ in the integrated irradiation dose. However, when the absorption region of the photo cation generator is extremely different from the spectrum of the light source or the liquid crystal material itself can absorb a light in the wavelength of the light source, the irradiation dose is not limited to the above range. In these cases, a method may be employed in which a suitable photo sensitizer or two or more kinds of photo cation generators having different absorption wavelengths are used.

The temperature at the time of the light irradiation needs to be within the range wherein the liquid crystal material exhibits a liquid crystal orientation. Furthermore, the light irradiation is preferably conducted at a temperature which is the Tg of the liquid crystalline material, or higher in order to conduct the curing effectively.

The liquid crystal material layer produced through the above-described processes becomes a sufficiently solid and strong film. More specifically, since the three-dimensional bond of the mesogen portion is archived by the curing reaction, the liquid crystal material layer (film) of the present invention is improved not only in heat-resistance (rise of the temperature at which the liquid crystal orientation is maintained) but also in mechanical strength such as resistance to scratch, wear and cracking. The present invention is of great significance in the industrial sense because it can achieve the directly-opposed purposes, i.e., the control of a liquid crystal orientation at ease and the improvements of the thermal/mechanical strength, at the same time.

The liquid crystal material layer wherein the liquid crystal orientation is fixed can be used as an optical film in the form in which the film remains supported on the alignment substrate (alignment substrate/(alignment layer)/liquid crystal film), in the form in which the film is transferred to a transparent substrate film or the like other than the alignment substrate (transparent substrate film/liquid crystal film), or in the form of a single layer of the liquid crystal film.

The liquid crystal orientation state which the liquid crystal material layer of the present invention will be able to assume can be controlled by properly selecting the side chain-type liquid crystalline polymeric substance and the structures of the other compounds constituting the liquid crystal material. The liquid crystal material layer of the present invention can assume a nematic orientation, a twisted nematic orientation, a cholesteric orientation, a nematic hybrid orientation, a smectic orientation, or a smectic C* orientation and an optical film wherein the orientation is fixed can be produced.

The liquid crystal film of the present invention can be used particularly as an optical film and mounted in a liquid crystal display. Optical films have various uses and are preferably used as optical retardation films, color compensation films, viewing angle improving films, circular polarizer films, and optical rotatory films.

For example, an optical film wherein a nematic or twisted nematic orientation is fixed functions as an optical retardation film and a compensation plate for an STN-, TN-, OCB-, or HAN-transmission or reflection type liquid crystal display. An optical film wherein a cholesteric or smectic C* orientation is fixed can be used as a polarizing reflective film for luminance enhancement, a reflection color filter, and various decoration films utilizing color variations of reflection light depending on viewing angles due to the selective reflection. An optical film wherein a smectic orientation is fixed can be used as a diffraction film. An optical film wherein a nematic hybrid orientation is fixed can be used as an optical retardation film or wave plate utilizing a retardation upon viewing from the front and a viewing angle improving film for a TN-type liquid crystal display utilizing the asymmetric nature of viewing angle dependency of retardation.

A side chain-type liquid crystalline polymeric substance can be easily produced by radical or anionic polymerization of the (meth)acrylic compound having an oxetanyl group of the present invention. The side-chain type liquid crystalline polymeric substance can be easily oriented at a low temperature and is cation-polymerized so as to polymerize and cross-link the oxetanyl group thereby obtaining a liquid crystal film with fixed orientation. The resulting liquid crystal film is enhanced in heat resistance and hardness and excellent in mechanical strength.

The present invention will be further described in the following examples, but the present invention should not be construed as being limited thereto.

The analyzing methods used in the examples are as follows.

(1) $^1$H-NMR Measurement

A compound was dissolved in deuterated chloroform and the composition was determined by means of $^1$H-NMR at 400 MHz (JNM-GX400 manufactured by Nippon Electronics Co., Ltd.).

(2) GPC Measurement

The GPC measurement was carried out by dissolving a compound in tetrahydrofuran and using 8020 GPC system manufactured by Tosoh corporation equipped with TSK-GEL, Super H1000, Super H2000, Super H3000, and Super H4000 which are connected in series and tetrahydrofuran as an eluent solvent. Polystyrene was used as a standard for calibration of molecular weight.

(3) Observation of Phase Behavior

The liquid crystal phase behavior was observed using an Olympus BH2 polarizing microscope while heating a sample on a Metler hot stage.

The phase transition temperature was measured using a differential scanning calorimeter DSC7 manufactured by Perkin Elmer Co.

(4) Parameter Measurement of Liquid Crystal Film

The retardation of a nematic orientation was measured using KOBRA manufactured by Otsuka Electronics Co., Ltd.

EXAMPLE 1

In accordance with Scheme 1 below, an acrylic compound having an oxetanyl group (acrylic compound 1) was synthesized using 3-ethyl-3-hydroxymethyloxetane (OXT-101, manufactured by Toagosei Co., Ltd.).

The $^1$H-NMR spectrum of the acrylic compound 1 is shown in FIG. 1. "x" in the figures indicates the peak of the impurities.

Scheme 1

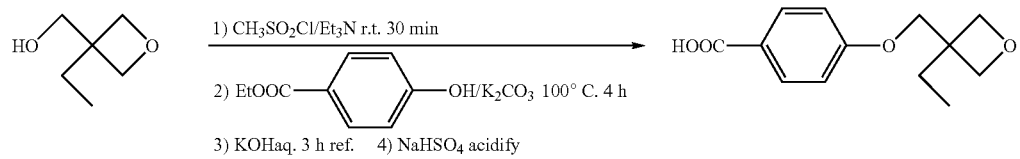

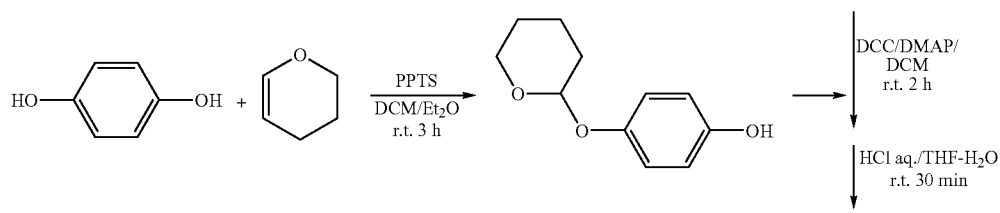

Figure 2:
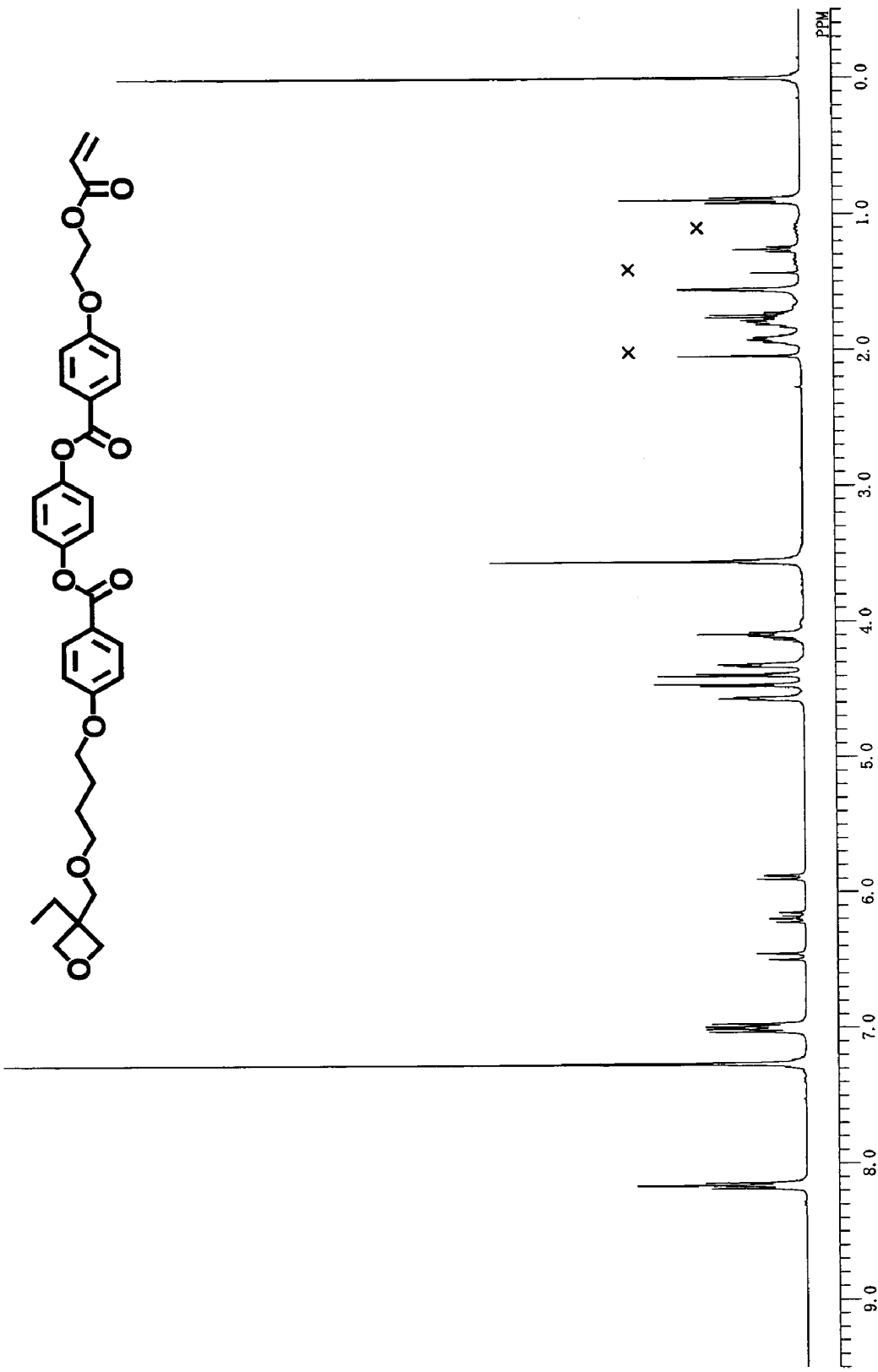
FIG. 2 shows the ¹H-NMR spectrum of the acrylic compound 2 obtained in Example 2.

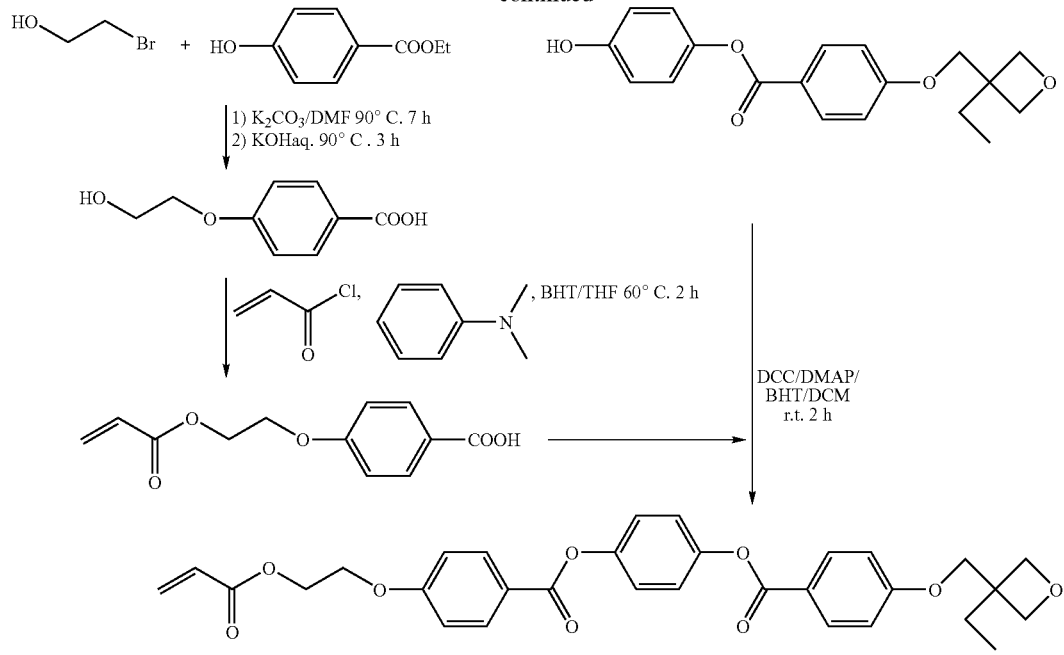
EXAMPLE 2
In accordance with Scheme 2 below, an acrylic compound having an oxetanyl group (acrylic compound 2) was synthesized using 3-ethyl-3-hydroxymethyloxetane (OXT-101, manufactured by Toagosei Co., Ltd).
The $^1$H-NMR spectrum of the acrylic compound 2 is shown in FIG. 2.
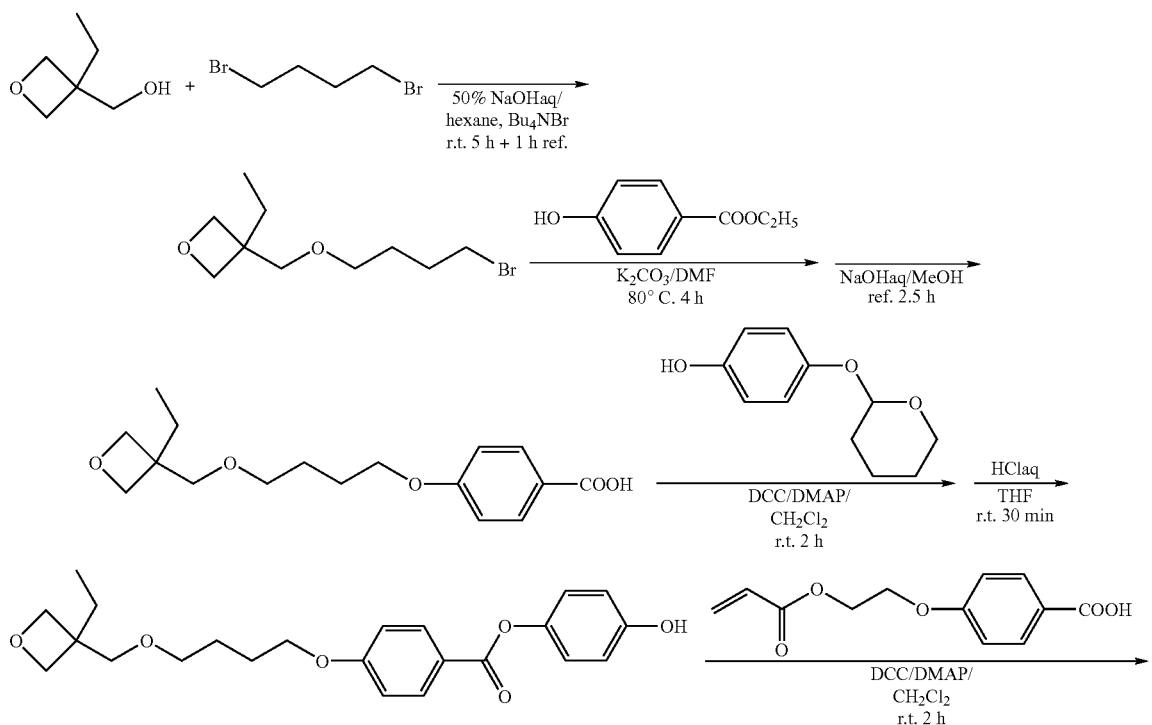

-continued

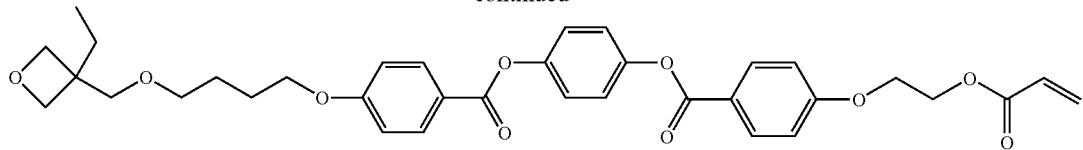

10

EXAMPLE 3

Figure 3:
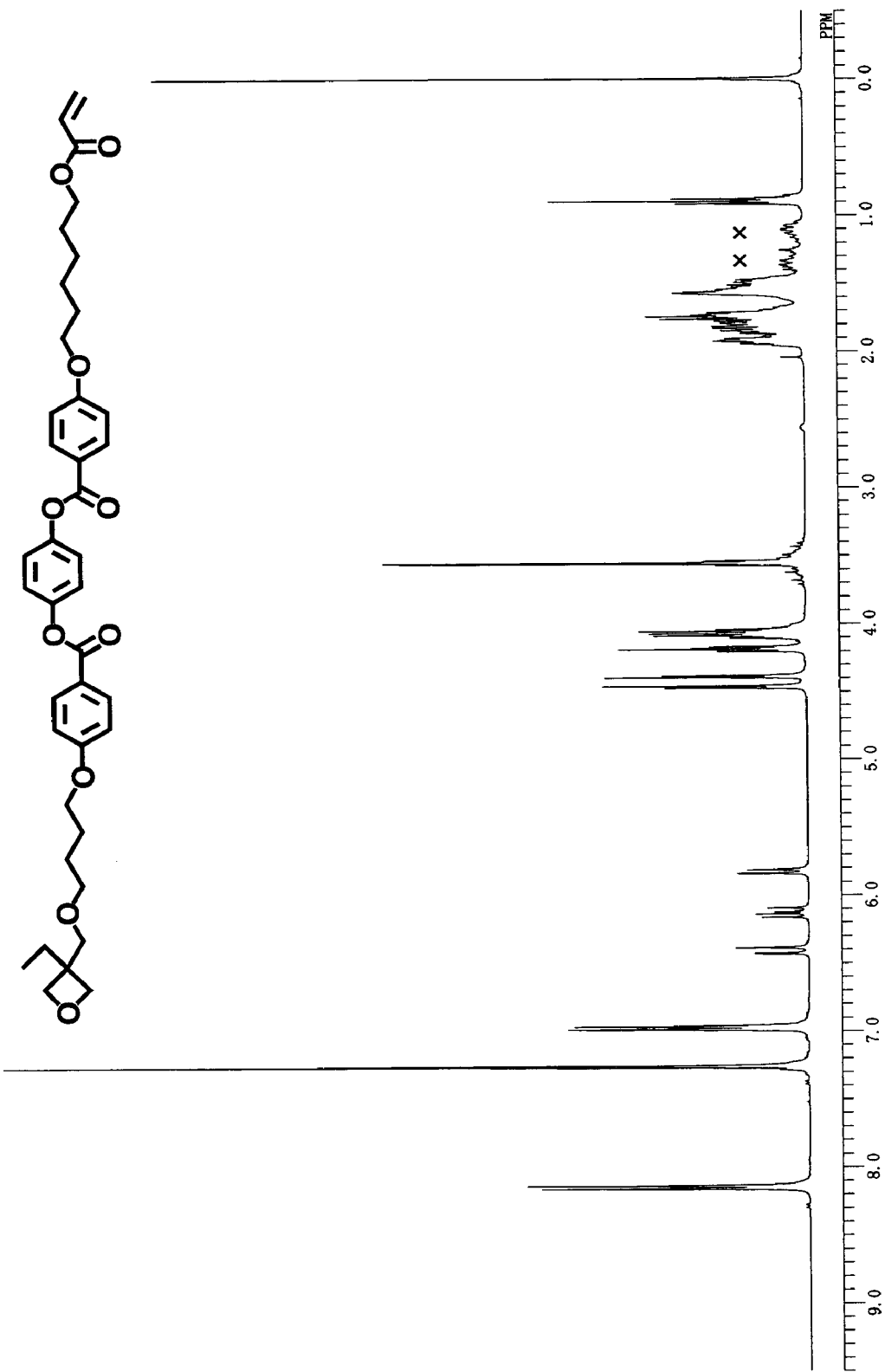
FIG. 3 shows the ¹H-NMR spectrum of the acrylic compound 3 obtained in Example 3.

In accordance with Scheme 3 below, an acrylic compound 3 having an oxetanyl group (acrylic compound 3) was synthesized. The ¹H-NMR spectrum of the acrylic compound 3 is shown in FIG. 3.

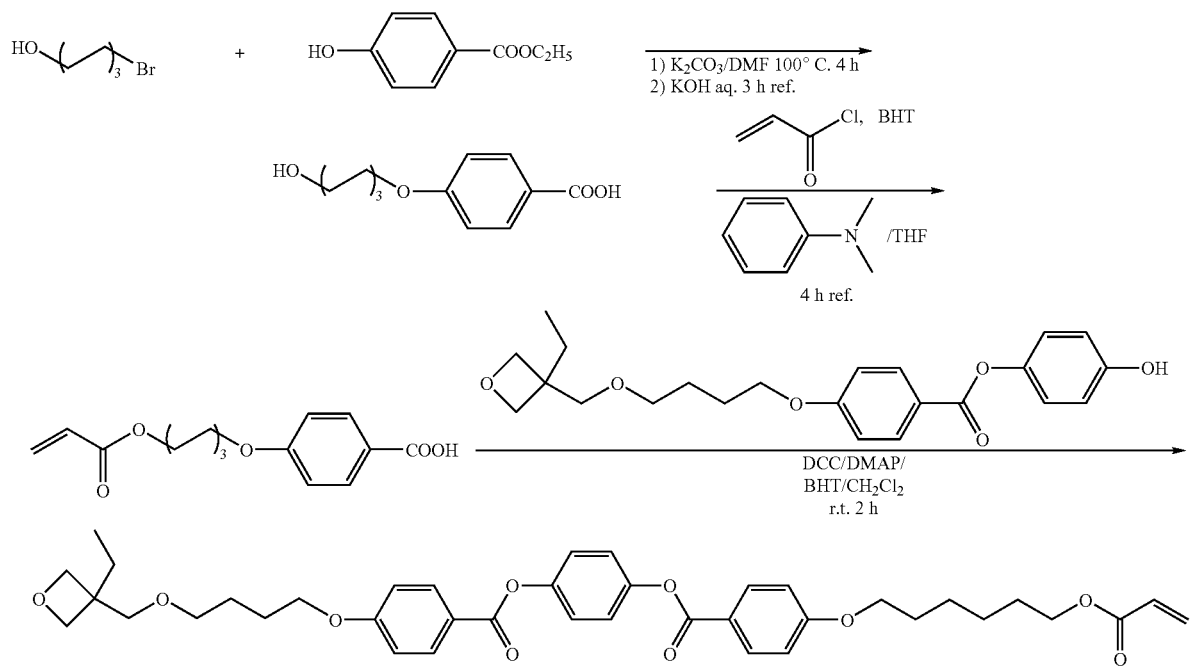

EXAMPLE 4

Figure 4:
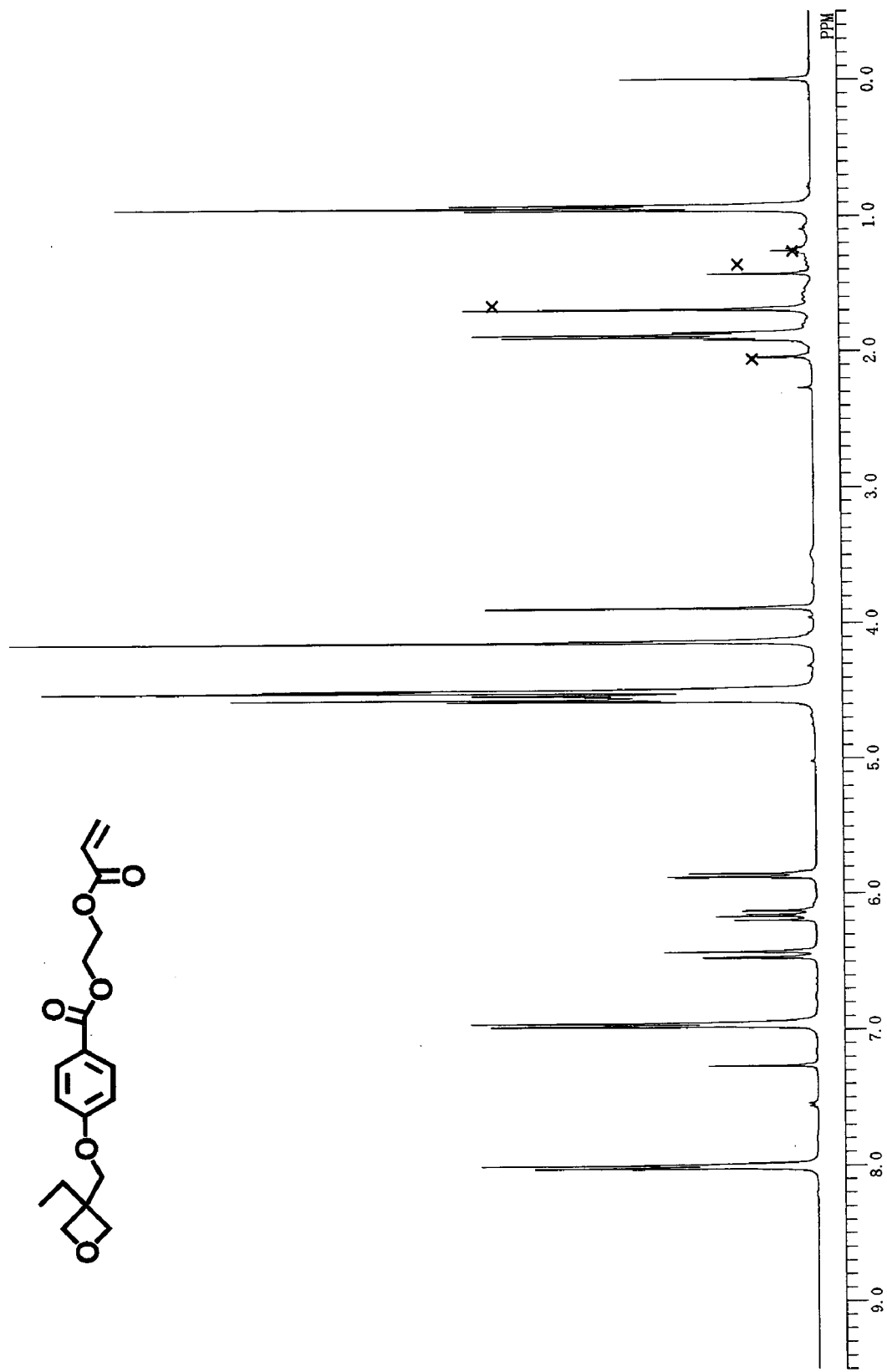
FIG. 4 shows the $^1$H-NMR spectrum of the acrylic compound 4 obtained in Example 4.

In accordance with Scheme 4 below, an acrylic compound 4 having an oxetanyl group (acrylic compound 4) was synthesized. The ¹H-NMR spectrum of the acrylic compound 4 is shown in FIG. 4.

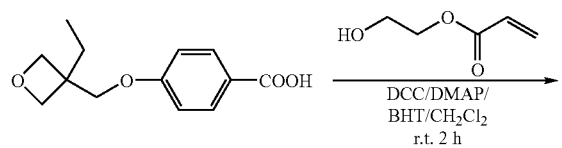

-continued

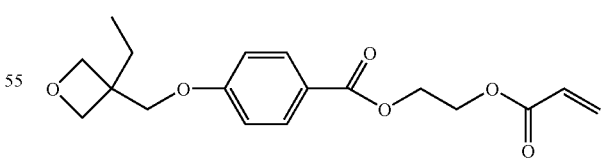

EXAMPLE 5

Figure 5:
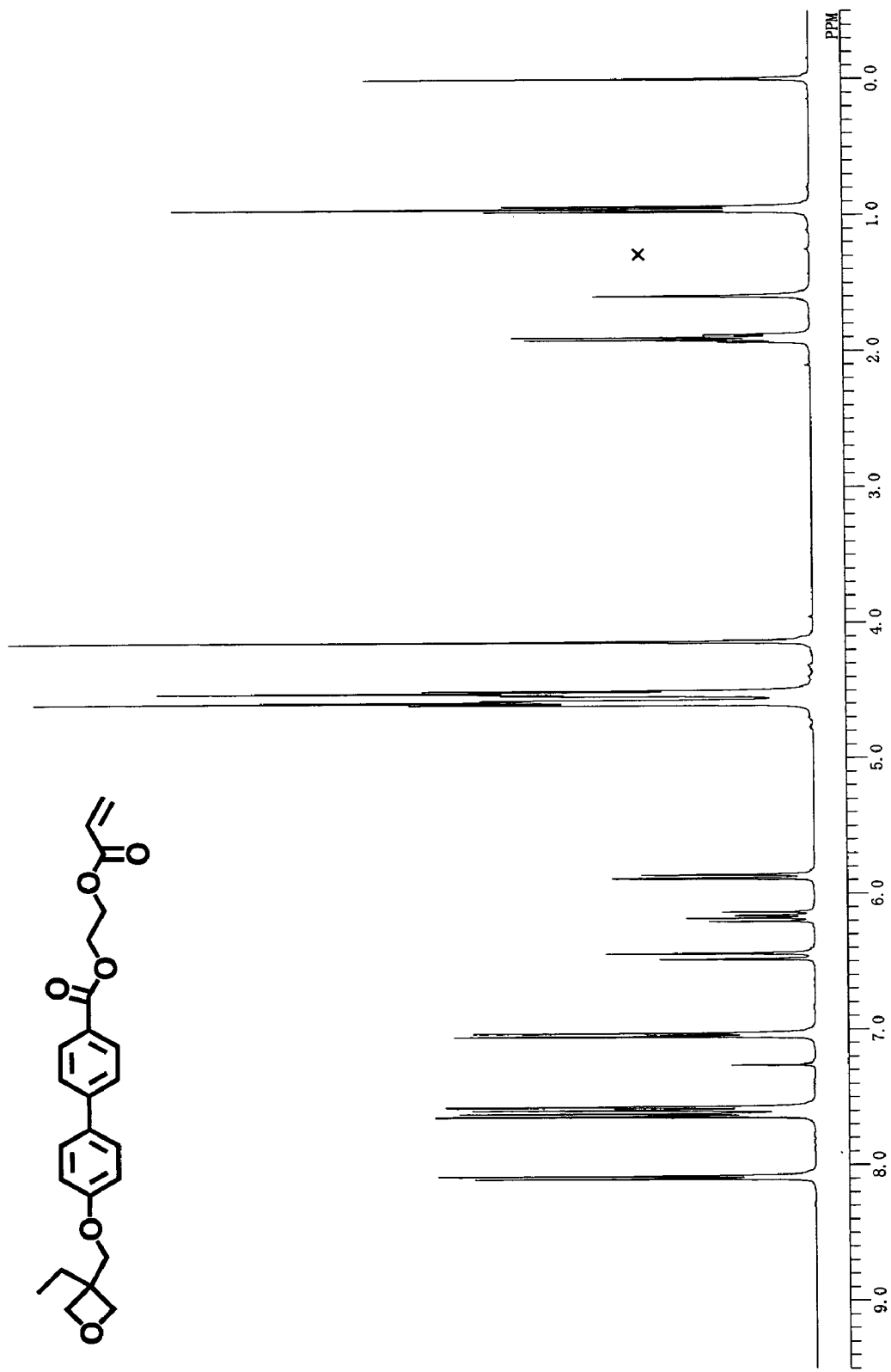
FIG. 5 shows the $^1$H-NMR spectrum of the acrylic compound 5 obtained in Example 5.

In accordance with Scheme 5 below, an acrylic compound 5 having an oxetanyl group (acrylic compound 5) was synthesized. The ¹H-NMR spectrum of the acrylic compound 5 is shown in FIG. 5.

Figure 6:
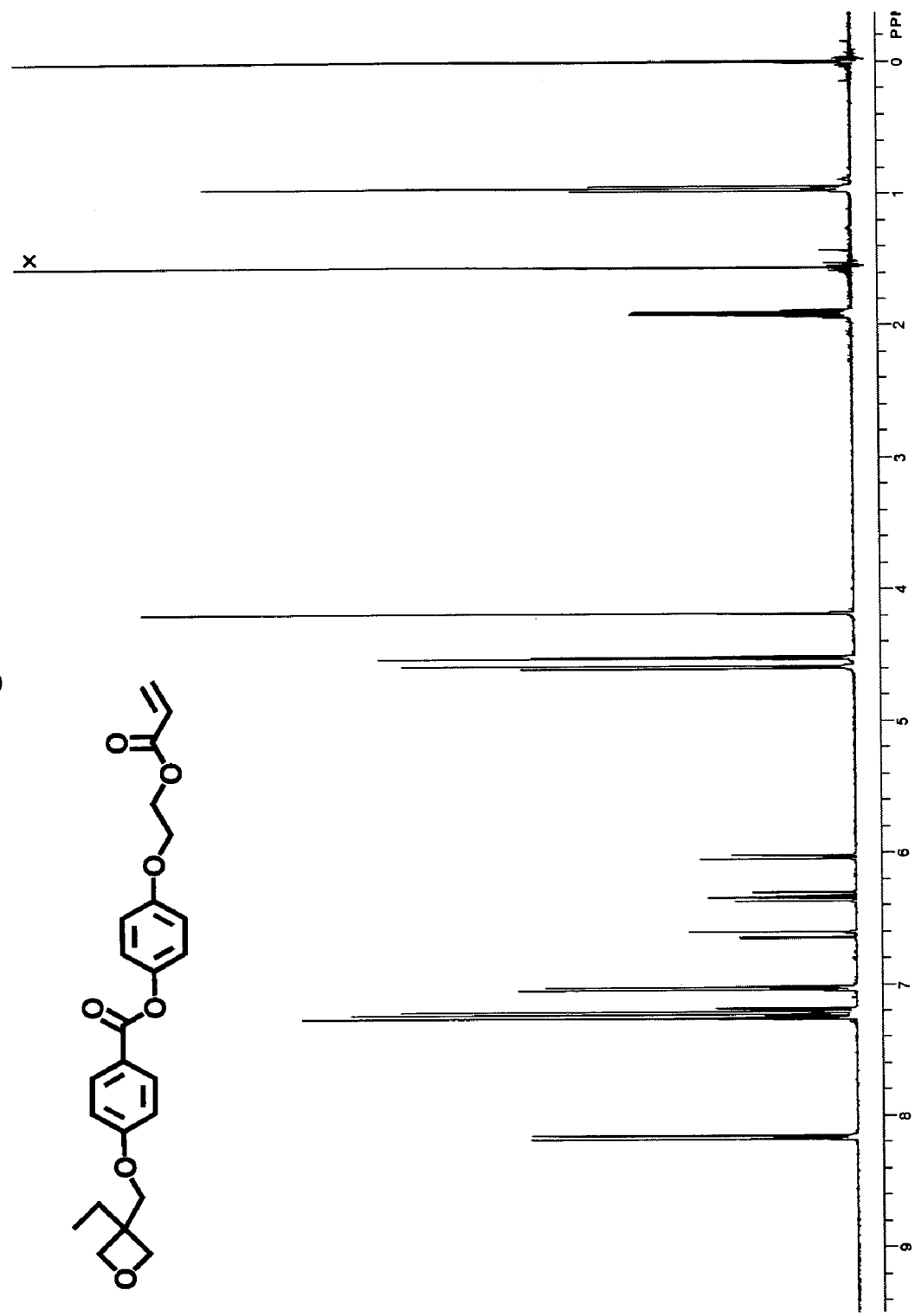
FIG. 6 shows the $^1$H-NMR spectrum of the acrylic compound 6 obtained in Example 6.

Scheme 5
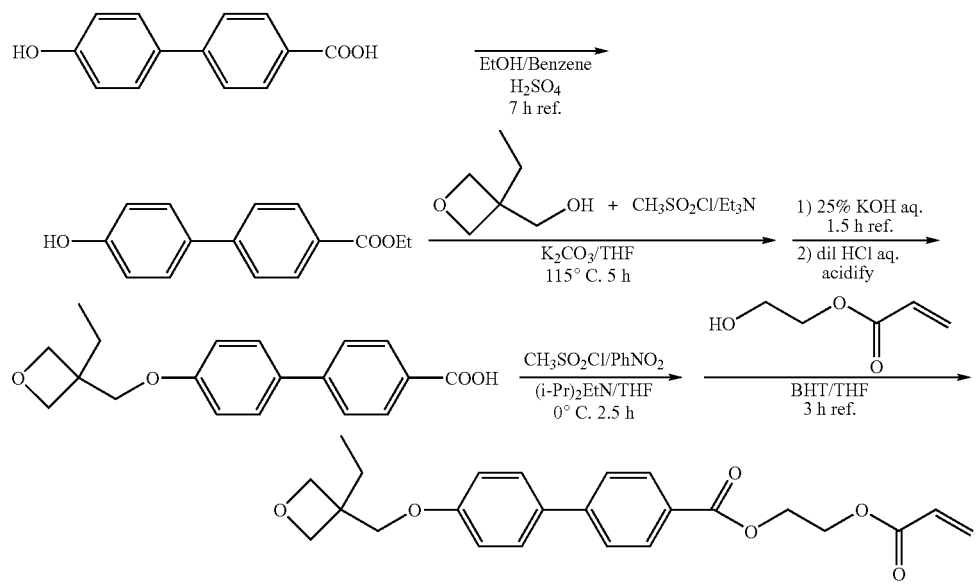
EXAMPLE 6
In accordance with Scheme 6 below, an acrylic compound 6 having an oxetanyl group (acrylic compound 6) was synthesized. The $^1$H-NMR spectrum of the acrylic compound 6 is shown in FIG. 6.
REFERENCE EXAMPLE 1
In accordance with Scheme 7 below, acrylic compounds (wherein m=1) and (wherein m=3) having no oxetanyl group
Scheme 6
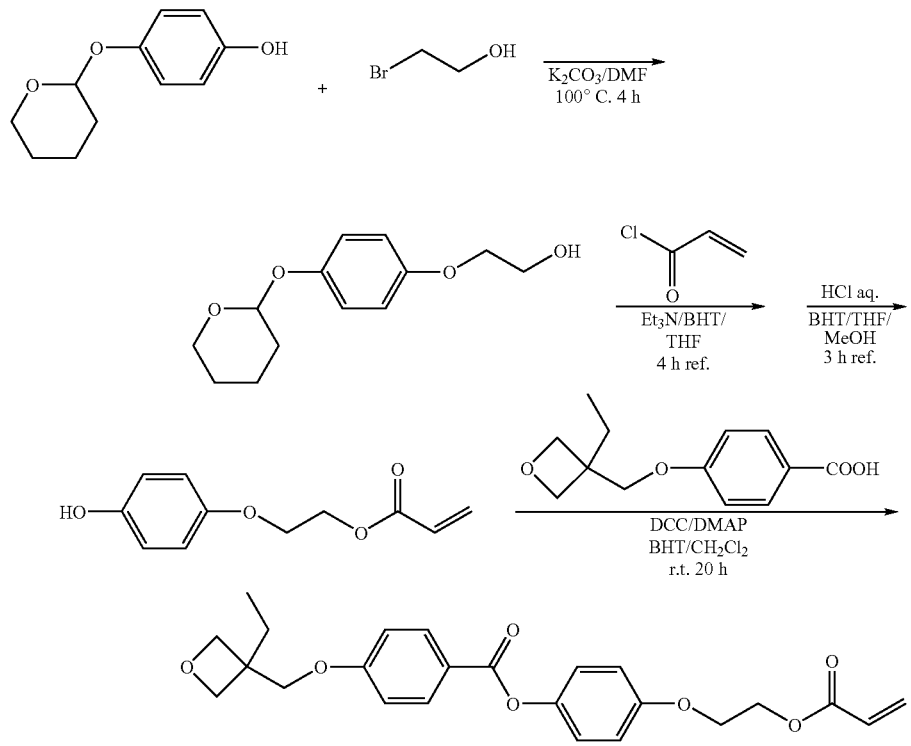

Figure 7:
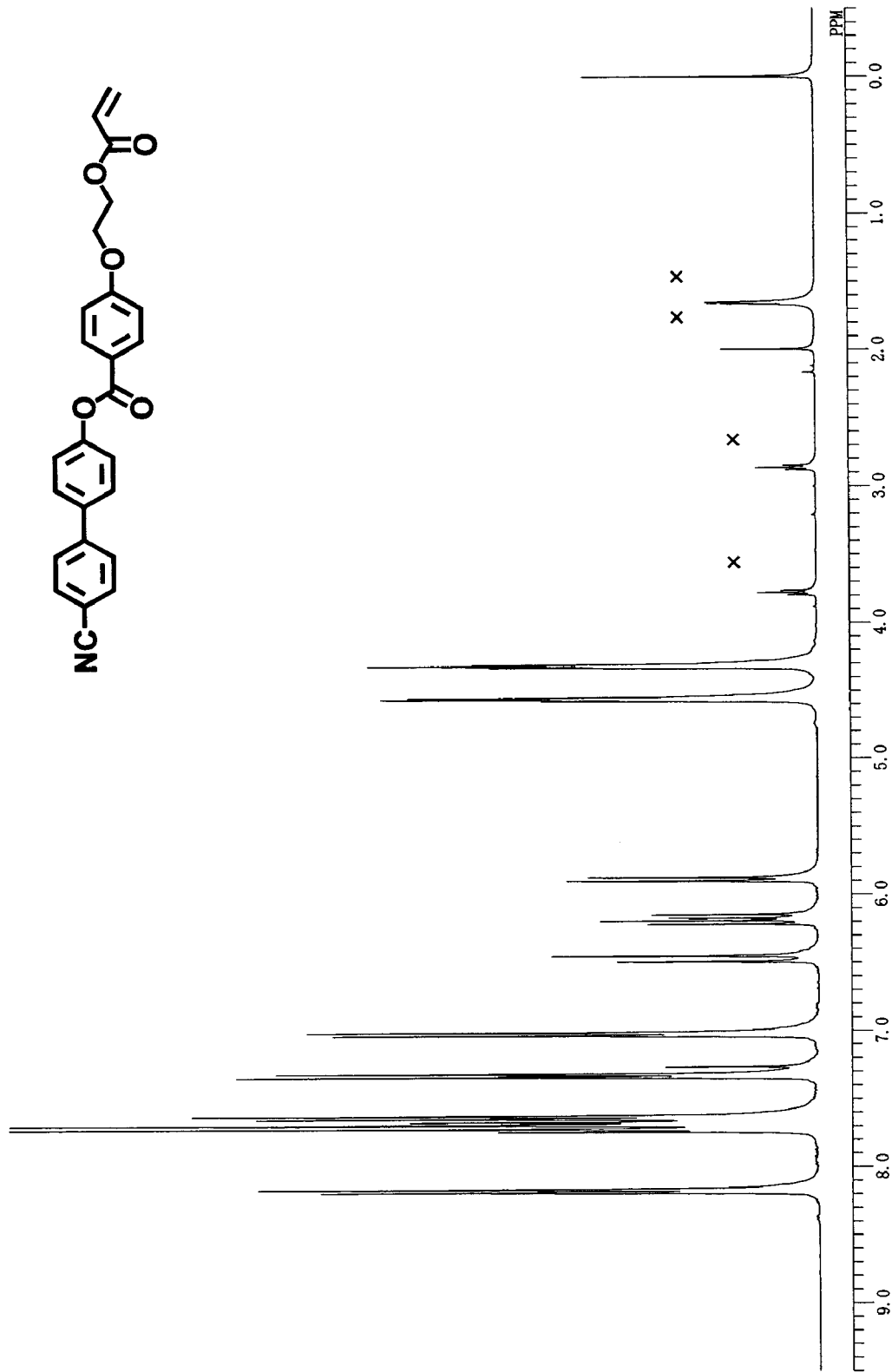
FIG. 7 shows the $^1$H-NMR spectrum of the acrylic compound 7 obtained in Reference Example 1.
Figure 8:
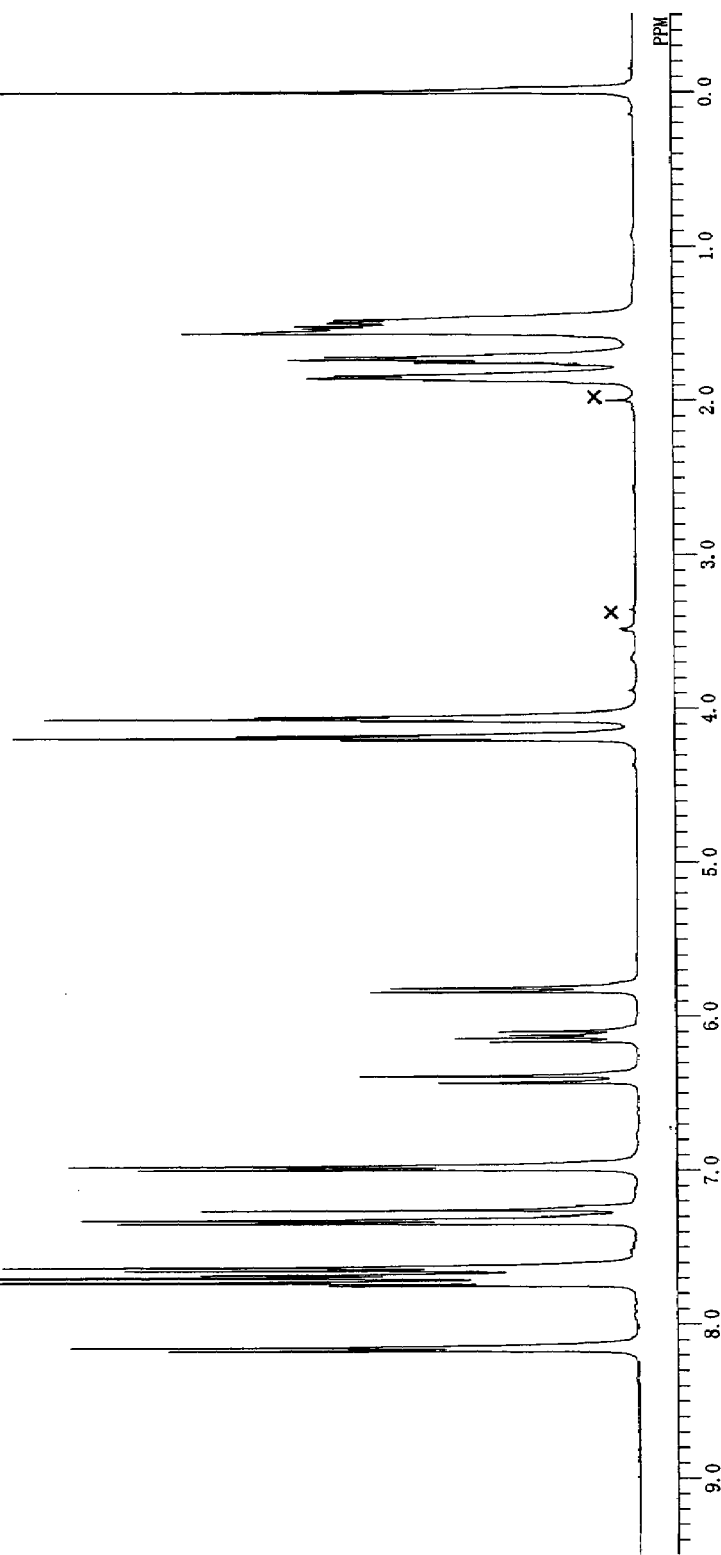
FIG. 8 shows the $^1$H-NMR spectrum of the acrylic compound 8 obtained in Reference Example 1.

(acrylic compounds 7 and 8) were synthesized. The $^1$H-NMR spectrum of each the acrylic compounds 7 and 8 is shown in FIGS. 7 and 8.

Scheme 7

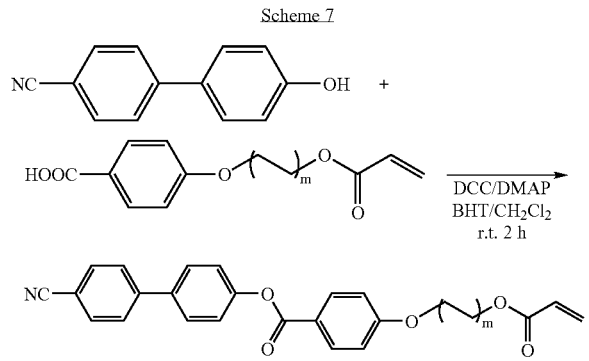

EXAMPLE 7

Synthesis of Side Chain-Type Liquid Crystalline Polyacrylates Having an Oxetanyl Group The acrylic compounds 1 to 8 were subjected to a radical-polymerization using 2,2'-azobisisobutylonitrile as an initiator and DMF as a solvent under a nitrogen atmosphere at a temperature of 90° C. for 6 hours and reprecipitated with methanol for purification thereby obtaining side chain-type liquid crystalline polyacrylates having an oxetanyl group (Polyacrylates 1 to 12).

REFERENCE EXAMPLE 2

Synthesis of Side Chain-Type Liquid Crystalline Polyacrylates Having No Oxetanyl Group With the same procedures of Example 7, side chain-type liquid crystalline polyacrylates having no oxetanyl group (Polyacrylates 13 and 14) were synthesized.

Table 1 below shows the formulations, molecular weight, Tg and phase behavior of each of Polyacrylates 1 to 14. In Table 1, "Sm", "Nm" and "Iso" indicate smectic phase, nematic phase, and isotropic phase, respectively. A phase behavior indicated by "phase (Sm)-temperature-phase (Nm)" also indicates that the polyacrylate exhibited a isotropic phase at a temperature of 250° C. or higher.

Figure 9:
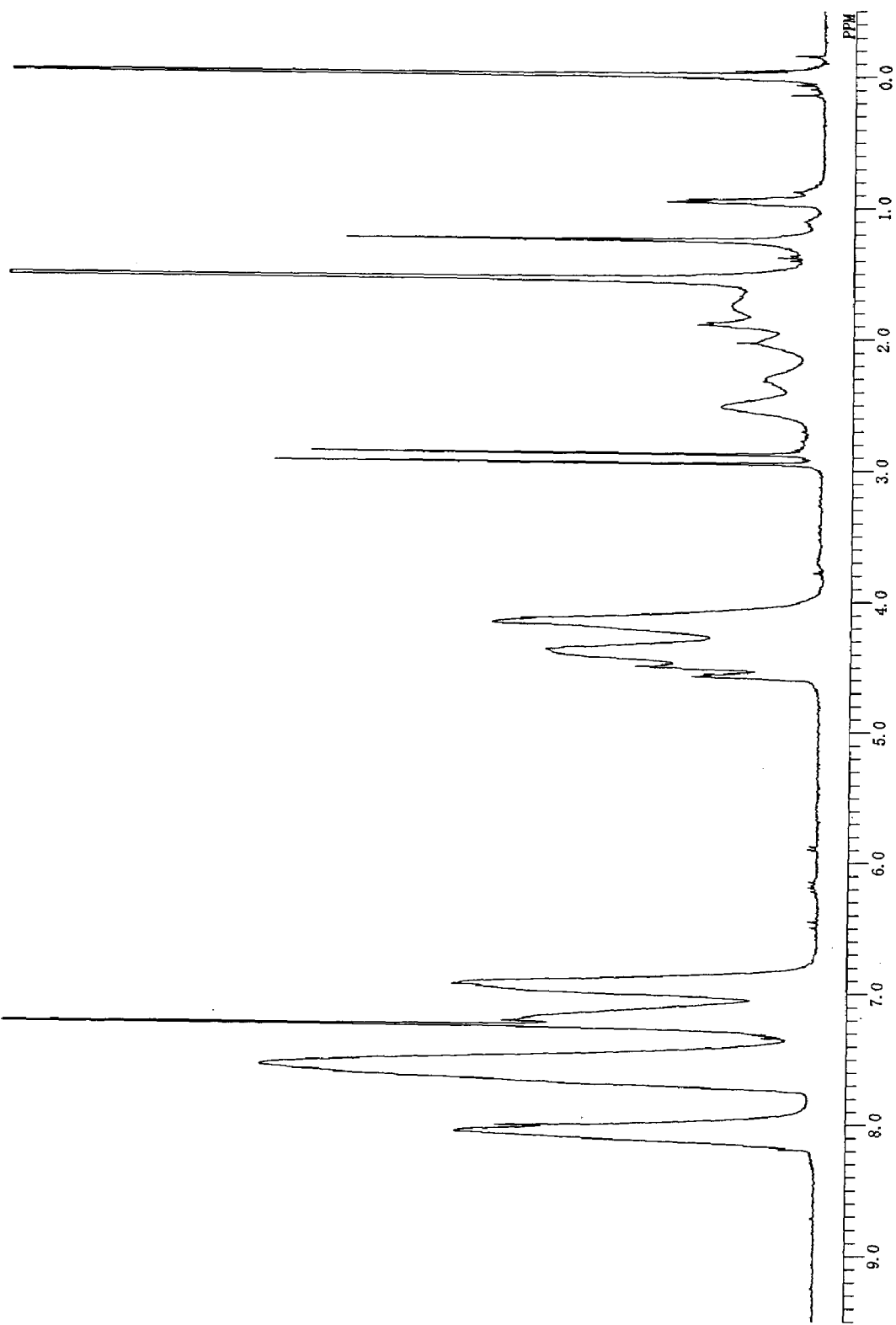
FIG. 9 shows the $^1$H-NMR spectrum of the side-chain type liquid crystalline polyacrylate 4 obtained in Example 7.
Figure 10:
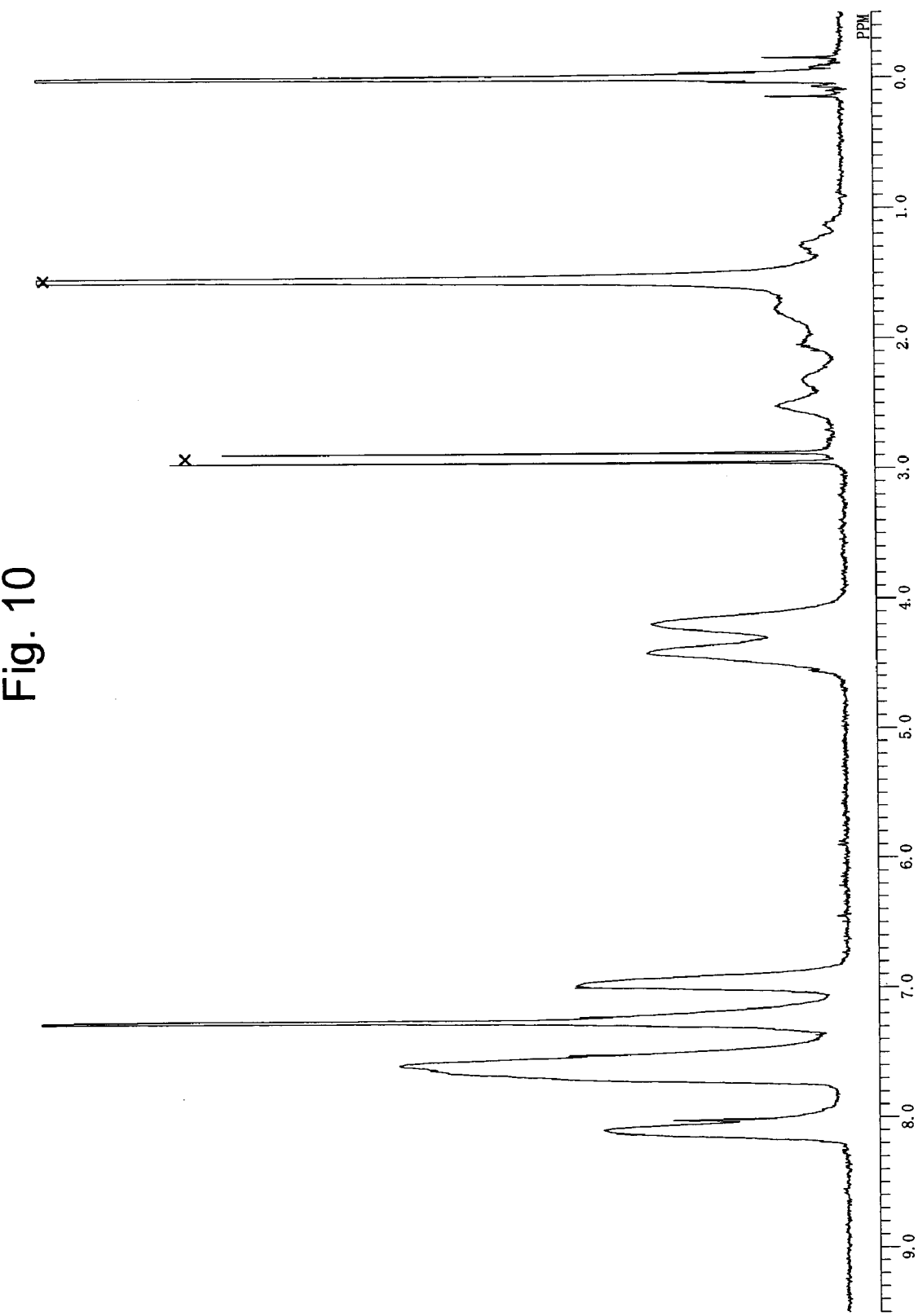
FIG. 10 shows the $^1$H-NMR spectrum of the side chain-type liquid crystalline polyacrylate 13 obtained in Reference Example 2.

FIGS. 9 and 10 show the $^1$H-NMR spectrums of Polyacrylates 4 and 13.

TABLE 1

| Polymer No. | Monomer Unit (molar ratio, percentage) | | | | | | | | Weight Average Molecular Weight | Tg (° C.) | Phase Behavior |
| --- | --- | --- | --- | --- | --- | --- | --- | --- | --- | --- | --- |
| | 1 | 2 | 3 | 4 | 5 | 6 | 7 | 8 | | | |
| 1 | 100 | | | | | | | | 39,600 | 81 | Sm-170° C.-Nm |
| 2 | 50 | | | | | | 50 | | 21,500 | 78 | Sm-152° C.-Nm |
| 3 | 20 | | | | | | 80 | | 9,700 | 81 | Sm-138° C.-Nm |
| 4 | 10 | | | | | | 90 | | 9,500 | 79 | Sm-109° C.-Nm |
| 5 | | 20 | | | | | 80 | | 21,400 | 71 | Sm |
| 6 | | 20 | | | | | | 80 | 6,100 | 61 | Sm-213° C.-Nm |
| 7 | | | 20 | | | | 80 | | 5,500 | 56 | Sm-140° C.-Nm |
| 8 | | | 20 | | | | 40 | 40 | 5,500 | 60 | Sm |
| 9 | | | 20 | | | | | 80 | 5,600 | 63 | Sm |
| 10 | | | | 50 | | | 50 | | 4,900 | 66 | Sm |
| 11 | | | | | 50 | | 50 | | 5,200 | 66 | Sm-123° C.-Nm |
| 12 | | | | | | 50 | 50 | | 9,500 | 74 | Sm-144° C.-Iso |
| 13 | | | | | | | 100 | | 6,600 | 74 | Nm |
| 14 | | | | | | | 50 | 50 | 7,900 | 59 | Sm-128° C.-Nm |

REFERENCE EXAMPLE 3

Synthesis of a Difunctional Oxetane Monomer

Figure 11:
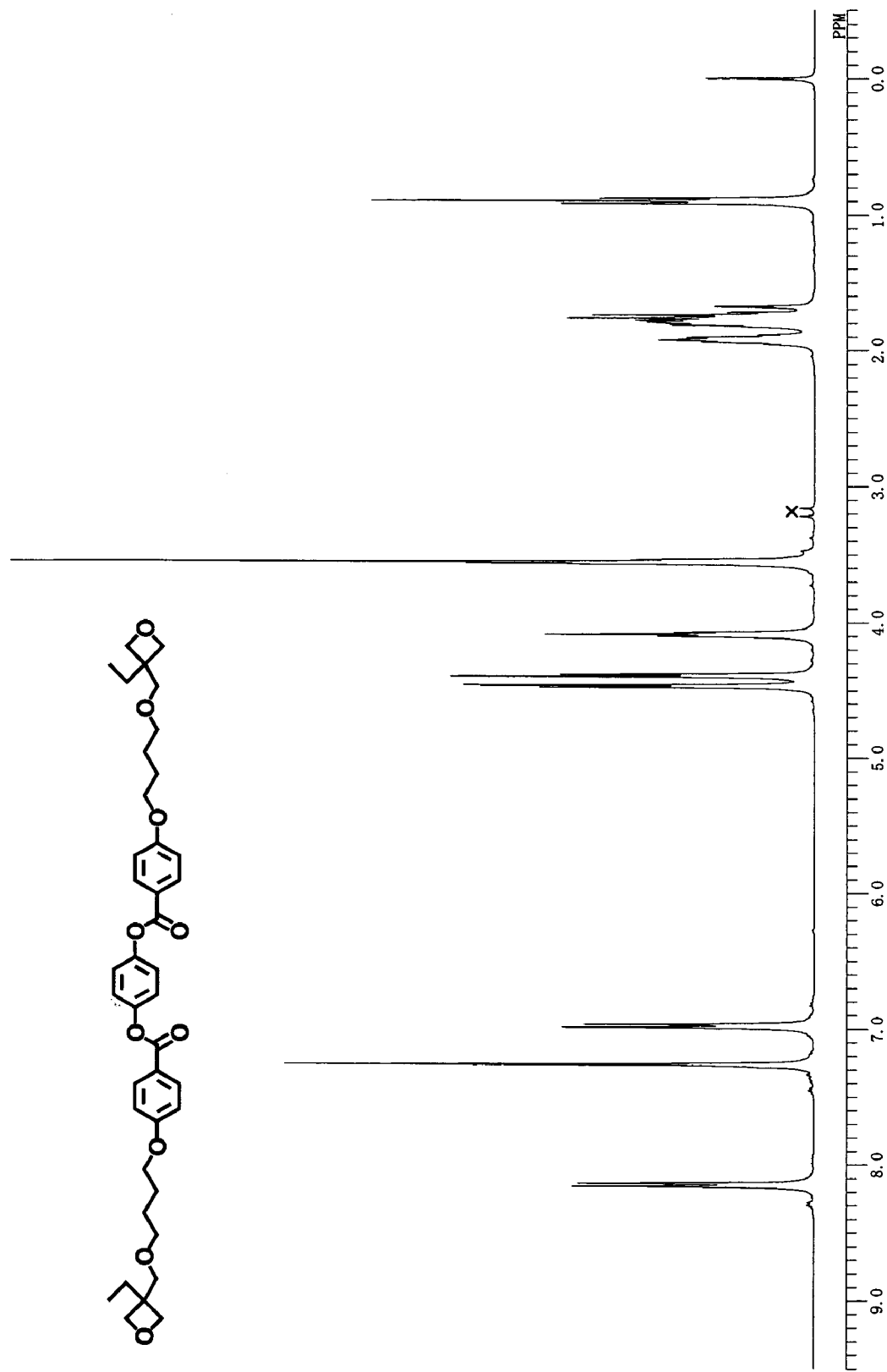
FIG. 11 shows the $^1$H-NMR spectrum of the difunctional oxetane monomer in Reference Example 3.

In accordance with Scheme 8, a difunctional oxetane monomer was synthesized. The $^1$H-NMR spectrum of the monomer is shown in FIG. 11.

From the DSC measurement and Metler observation, it was found that the monomer exhibited the phase behavior represented by "crystal-69° C.-nematic phase-95° C.-isotropic phase".

Scheme 8

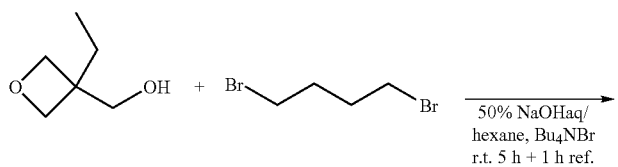

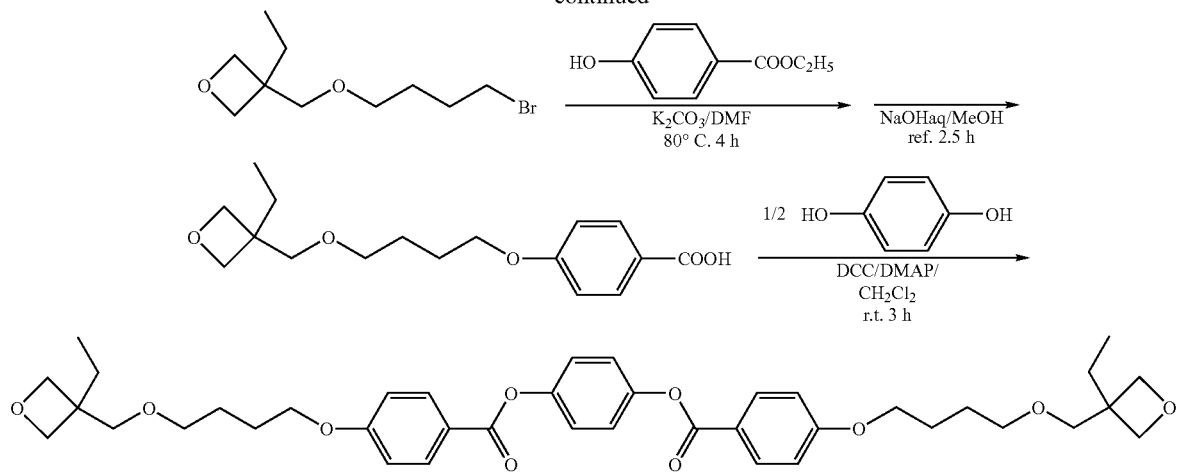

EXAMPLE 8

Preparation of a Liquid Crystal Film Using a Side Chain-Type Liquid Crystalline Polyacrylate (Polyacrylate 4)

1.0 g of Polyacrylate 4 obtained in Example 7 was dissolved in 9 ml of cyclohexane and to the solution was added in a dark place 0.05 g of a propylene carbonate solution with 50% triaryllsulfoniumhexafluoroantimonate (a reagent manufactured by Aldrich Co.), followed by filtration of the insolubles with a polytetrafluoroethylene filter with a pore size of 0.45 µm thereby preparing a solution of a liquid crystal material.

The solution was spin-coated over a 50 µm thickness polyethylene naphthalate film "Teonex Q-51" manufactured by TEIJIN Limited whose surface had been subjected to a rubbing treatment with a rayon cloth and then dried at a temperature of 60° C. on a hot plate. The resulting liquid crystal material layer on the film was irradiated with an ultraviolet light of the integrated irradiation dose of 450 mJ/cm$^2$ from a high-pressure mercury lamp under an air atmosphere while heating at a temperature of 150° C. and then cooled thereby obtaining a cured liquid crystal material layer.

Since the polyethylene naphthalate film used as a substrate is large in birefringence and thus not preferred as an optical film, the resulting film (the liquid crystal material layer) was transferred via an ultraviolet curing-type adhesive "UV-1394" manufactured by Toagosei Co., Ltd. onto a triacetylcellulose film (TAC) thereby obtaining an optical film. More specifically, UV-1394 with a thickness of 5 µm was coated over the cured liquid crystal material layer on the film and laminated with a TAC film. After the laminate was subjected to an irradiation of ultraviolet light of 400 mJ/cm$^2$ from the TAC film side so as to cure the adhesive, the polyethylene naphthalate film (substrate) was peeled off.

As a result of observations of the resulting optical film using a polarizing microscope, it was confirmed that it exhibited a monodomain uniform nematic liquid crystal orientation without the occurrence of disclination and the retardation was 115 nm. Only the liquid crystal material portion was scrapped off and the glass transition temperature thereof was measured using a DSC. As a result, it was found to be 95° C. The pencil hardness of the liquid crystal material surface of the film was on the order of 2H and thus it was confirmed that the film had a sufficient hardness.

The optical film was laminated via a non-carrier pressure sensitive adhesive onto a 2 mm thickness glass plate and over the film was laminated a polarizer (SQW-862 manufactured by Sumitomo Chemical Co., Ltd.) such that the rubbing axis of the liquid crystal layer is aligned with the absorption axis of the polarizer. This sample was observed through the polarizer on a backlight and found to be a uniform film. After the sample was kept in a thermostat whose temperature was set at 80° C., for 24 hours, it was removed therefrom and similarly observed. As a result, neither change nor disorder in the liquid crystal orientation was observed.

As described above, it was found that the use of Polyacrylate 4 made it possible to produce a film which exhibits an excellent liquid crystal orientability and is improved in thermal stability and strength after fixation of the liquid crystal orientation.

REFERENCE EXAMPLE 4

Preparation of a Liquid Crystal Film Using a Side Chain-Type Liquid Crystalline Polyacrylate (Polyacrylate 13)

1.0 g of Polyacrylate 13 obtained in Reference Example 2 was dissolved in 9 ml of cyclohexane, followed by filtration of the insolubles with a polytetrafluoroethylene filter with a pore size of 0.45 µm thereby preparing a solution of a liquid crystal material.

The solution was spin-coated over a 50 µm thickness polyethylene naphthalate film "Teonex Q-51" manufactured by TEIJIN Limited whose surface had been subjected to a rubbing treatment with a rayon cloth and then dried at a temperature of 60° C. on a hot plate. The resulting liquid crystal material layer on the film was heated at a temperature of 150° C. for 5 minutes and then quenched to room temperature thereby obtaining a liquid crystal material layer.

Since the polyethylene naphthalate film used as a substrate is large in birefringence and thus not preferred as an optical film, the resulting film (liquid crystal material layer) was transferred via an ultraviolet curing-type adhesive "UV-1394" manufactured by Toagosei Co., Ltd. onto a triacetylcellulose film (TAC) thereby obtaining an optical film. More specifically, UV-1394 with a thickness of 5 µm was coated over the cured liquid crystal material layer on the film and laminated with a TAC film. After the laminate was subjected to an irradiation of ultraviolet light of 400 mJ/cm² from the TAC film side so as to cure the adhesive, the polyethylene naphthalate film (substrate) was peeled off.

As a result of observations of the resulting optical film using a polarizing microscope, it was confirmed that it exhibited a monodomain uniform nematic liquid crystal orientation without the occurrence of disclination and the retardation was 100 nm. However, after only the liquid crystal material portion was scrapped off and the glass transition temperature thereof was measured using a DSC, it was found to be 80° C. which is low. The pencil hardness of the liquid crystal material surface of the film was on the order of B and thus it was confirmed that the film was too soft to be used as an optical film.

The film was laminated via a non-carrier pressure sensitive adhesive onto a 2 mm thickness glass plate and over the film was laminated a polarizer (SQW-862 manufactured by Sumitomo Chemical Co., Ltd.) such that the rubbing axis of the liquid crystal layer is aligned with the absorption axis of the polarizer. This sample was observed through the polarizer on a backlight and found to be a uniform film. After the sample was kept in a thermostat whose temperature was set at 80° C., for 24 hours, it was removed therefrom and similarly observed. It was found that the film had voids at peripheries due to the disordered liquid crystal orientation.

EXAMPLE 9

Preparation of a Liquid Crystal Film Using a Side Chain-Type Liquid Crystalline Polyacrylate (Polyacrylate 4)

0.8 g of Polyacrylate 4 obtained in Example 7 and 0.2 g of the difunctional oxetane monomer obtained in Reference Example 3 were dissolved in 9 ml of cyclohexane and to the solution was added in a dark place 0.05 g of a propylene carbonate solution with 50% triallylsulfoniumhexafluoroantimonate (a reagent manufactured by Aldrich Co.), followed by filtration of the insolubles with a polytetrafluoroethylene filter with a pore size of 0.45 μm thereby preparing a solution of a liquid crystalline material.

The solution was spin-coated over a 100 μm thickness polyimide film "KAPTON" manufactured by Du Pont Co. whose surface had been subjected to a rubbing treatment with a rayon cloth and then dried at a temperature of 60° C. on a hot plate. The resulting liquid crystal material layer on the film was irradiated with an ultraviolet light of the integrated irradiation dose of 450 mJ/cm² from a high-pressure mercury lamp under an air atmosphere while heating at a temperature of 150° C. and then cooled thereby obtaining a cured liquid crystal material layer.

Since the polyimide film used as a substrate was brown and thus not preferred as an optical film, the resulting film (liquid crystal material layer) was transferred via an ultraviolet curing-type adhesive "UV-1394" manufactured by Toagosei Co., Ltd. onto a triacetylcellulose film (TAC) thereby obtaining an optical film. More specifically, UV-1394 with a thickness of 5 μm was coated over the cured liquid crystal material layer on the film and laminated with a TAC film. After the laminate was subjected to an irradiation of ultraviolet light of 400 mJ/cm² from the TAC film side so as to cure the adhesive, the polyimide film (substrate) was peeled off.

As a result of observations of the resulting optical film using a polarizing microscope, it was confirmed that it exhibited a monodomain uniform nematic hybrid liquid crystal orientation without the occurrence of disclination and the retardation viewed from the front was 115 nm. The retardation viewed from a direction obliquely at an angle of 40° from the vertical along the rubbing axis was 141 nm, while that from the opposite angle, i.e., −40° was 53 nm and asymmetric to the 40° retardation. Furthermore, there was no point wherein the retardation was 0 nm at any angle. From these observations, it was found that the film exhibited a nematic hybrid orientation structure.

Furthermore, only the liquid crystal material portion was scrapped off and the glass transition temperature thereof was measured using a DSC. As a result, the Tg was not observed.

The optical film was laminated via a non-carrier pressure sensitive adhesive onto a 2 mm thickness glass plate and over the film was laminated a polarizer (SQW-862 manufactured by Sumitomo Chemical Co., Ltd.) such that the rubbing axis of the liquid crystal layer is aligned with the absorption axis of the polarizer. This sample was observed through the polarizer on a backlight and found to be a uniform film. After the sample was kept in a thermostat whose temperature was set at 80° C., for 24 hours, it was removed therefrom and similarly observed. As a result, neither change nor disorder in the liquid crystal orientation was observed.

The pencil hardness of the liquid crystal material surface of the film was on the order of 2H and thus it was confirmed that the film had a sufficient hardness. As described above, it was found that the use of Polyacrylate 4 made it possible to produce a film which exhibits an excellent liquid crystal orientability and is improved in thermal stability and strength after fixation of the liquid crystal orientation.

EXAMPLE 10

Figure 12:
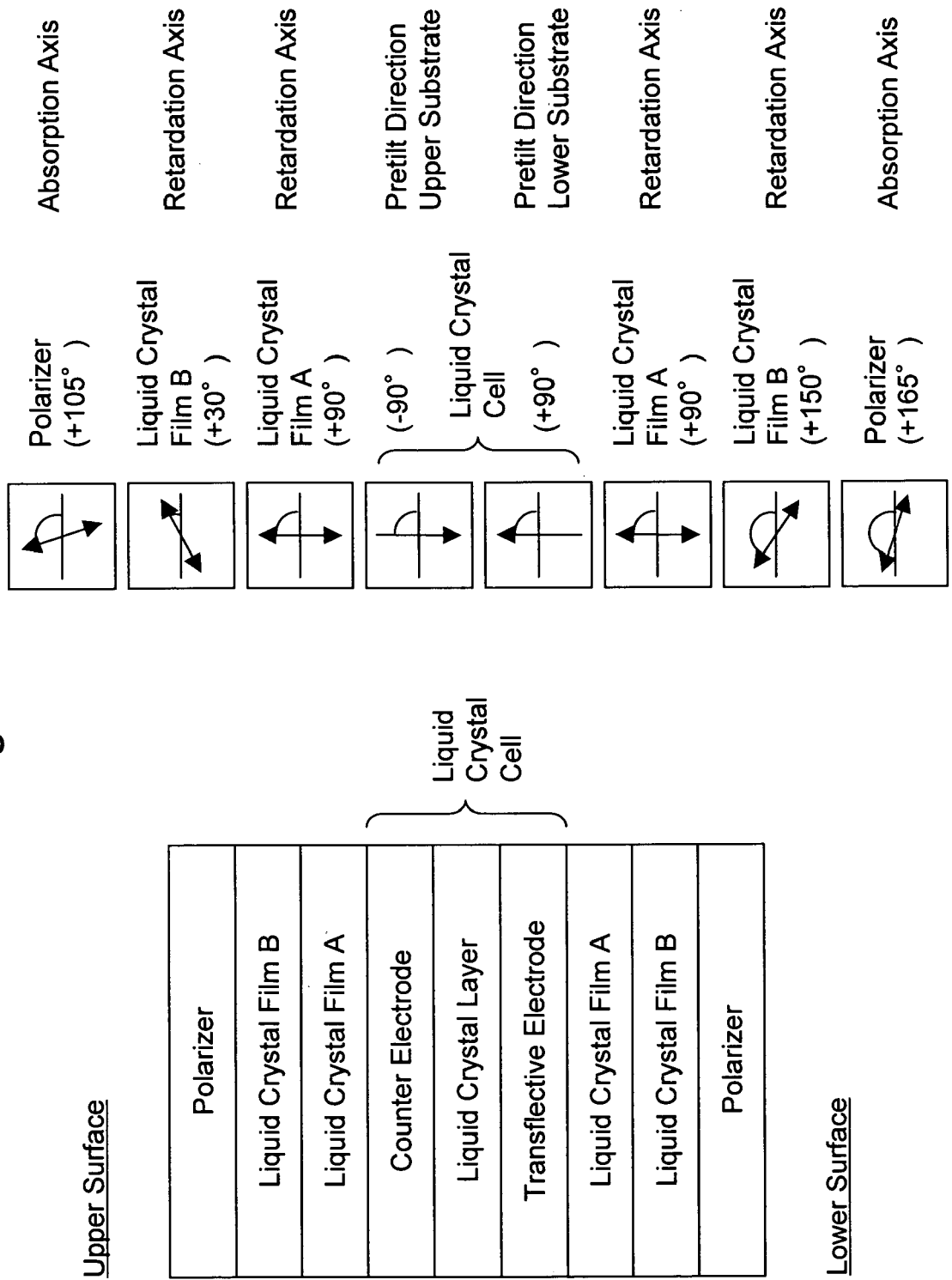
FIG. 12 is a schematic view showing the axial arrangement of each of the components constituting the liquid crystal display used in Example 10.

The optical film with a retardation of 115 nm obtained in Example 8 (hereinafter referred to "optical film A") and an optical film with a retardation of 265 nm obtained by the same procedure of Example 8 except that thickness of the liquid crystal material layer (hereinafter referred to "optical film B") was changed were used in combination as a wide bandwidth λ/4 plate and assembled with a transflective TFT-TNECB-type liquid crystal cell with a reflector thereby producing a liquid crystal display with the arrangement shown in FIG. 12. The liquid crystal cell contained ZLI-1695 manufactured by Merck Ltd as a liquid crystal material which had been formed into a homogenously-oriented liquid crystal layer with a thickness of 5 λm. The pretilt angle at the cell interface was 2°, while the Δnd of the liquid crystal cell was 310 nm. As a polarizer, SQW-862 manufactured by Sumitomo Chemical Co., Ltd. was used.

As a result, it was confirmed that CR=8, i.e., an excellent white and black was achieved.

EXAMPLE 11

Figure 13:
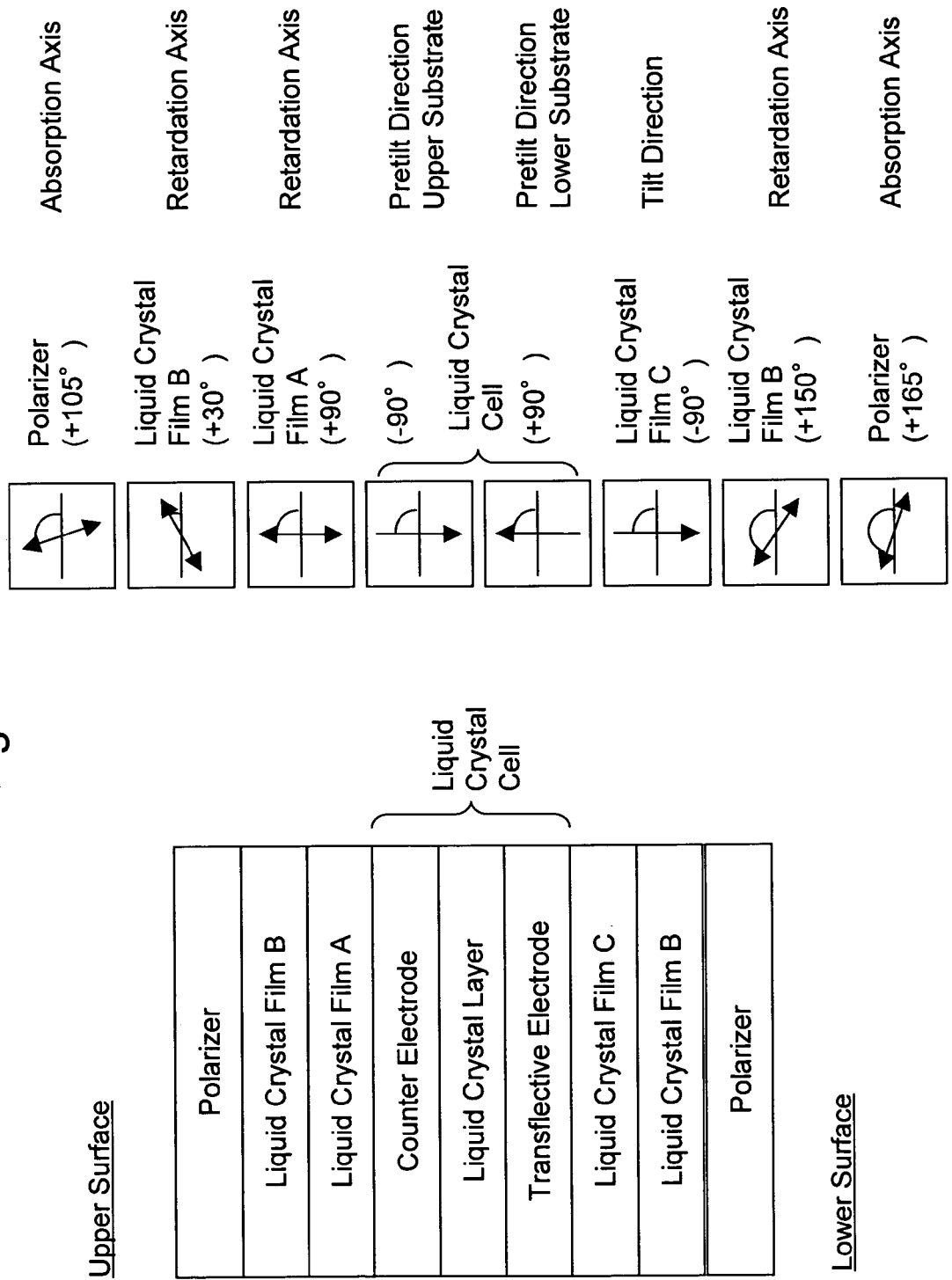
FIG. 13 is a schematic view showing the axial arrangement of each of the components constituting the liquid crystal display used in Example 11.

Wide bandwidth λ/4 plates were formed with the optical film A, the optical film with a front retardation of 115 nm and obtained in Example 9 (hereinafter referred to as "optical film C"), and the optical film 12 obtained in Example 10 and assembled with a TFT-transflective ECB-type liquid crystal cell with a reflector thereby producing a liquid crystal display with the arrangement shown in FIG. 13. The liquid crystal cell contained ZLI-1695 manufactured by Merck Ltd as a liquid crystalline material which had been formed into a homogenously-oriented liquid crystal layer with a thickness of 5 μm. The pretilt angle at the cell interface was 2°, while the Δ nd of the liquid crystal cell was 310 nm. As a polarizer, SQW-862 manufactured by Sumitomo Chemical Co., Ltd. was used.

As a result, it was confirmed that CR=8, i.e., an excellent white and black was achieved. Furthermore, it was also confirmed that a wider viewing angle can be obtained with this display than that of Example 10.

The invention claimed is:

1. A (meth)acrylic compound having an oxetanyl group represented by the formula

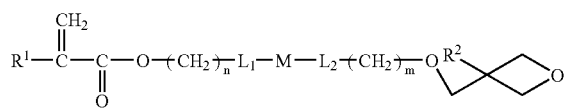

(1)

wherein $R^1$ is hydrogen or methyl, $R^2$ is hydrogen, methyl, or ethyl, $L_1$ and $L_2$• each are selected from a single bond, —O—, —O—CO—, and —CO—O—, M represents a formula selected from formulas (2), (3) and (4) below, and n and m are each independently an integer from 0 to 10:

—$P_1$—$L_3$—$P_2$—$L_4$—$P_3$—  (2)

—$P_1$—$L_3$—$P_3$—  (3)

—$P_3$—  (4)

wherein $P_1$ and $P_2$ are each independently a group selected from formulas (5) below, $P_3$ is a group selected from formulas (6) below, and $L_3$ and $L_4$ are each independently selected from a single bond, —CH=CH—, —C≡C—, —O—, —O—CO— and —CO—O—

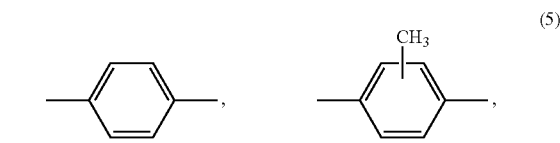

(5)

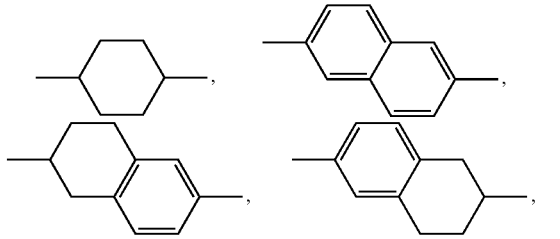

(6)

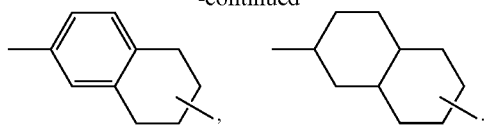

2. A side chain-type liquid crystalline polymeric substance obtained by homopolymerizing the (meth)acrylic portion of the (meth)acrylic compound having an oxetanyl group as defined in claim 1 or copolymerizing same with another (meth)acrylic compound.

3. The side chain-type liquid crystalline polymeric substance according to claim 2 which has a unit represented by formula (7) below derived from the (meth)acrylic compound having an oxetanyl group:

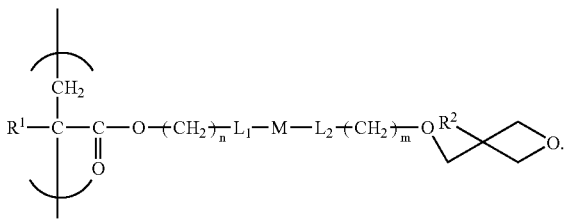

(7)

4. The side chain-type liquid crystalline polymeric substance according to claim 3 which contains a unit of said formula (7) in an amount of 5 to 100 percent by mol.

5. The side chain-type liquid crystalline polymeric substance according to claim 2 wherein the weight-average molecular weight is from 2,000 to 100,000.

6. A liquid crystal material which contains the side-chain type liquid crystalline polymeric substance as defined in claim 2 in an amount of 10 percent by mass or more.

7. The liquid crystal material according to claim 6 which further contains a photo cationic initiator and/or a thermal cationic initiator.

8. A liquid crystal film which is formed by fixing the orientation state of the liquid crystal material as defined in claim 6.

9. A method of producing a liquid crystal film wherein the liquid crystal material as defined in claim 6 is developed over an alignment substrate so as to align the liquid crystal material in a liquid crystal orientation state, followed by fixing the orientation by light irradiation and/or a heat treatment.

10. The method of producing a liquid crystal film according to claim 9 wherein said orientation state is one obtained by fixing an orientation state selected from the group consisting of nematic, twisted nematic, cholesteric, and nematic hybrid orientations.

11. An optical film which comprises the liquid crystal film as defined in claim 8.

12. The optical film according to claim 11 which is selected from the group consisting of a retardation film, a color compensation film, a viewing angle improving film, a circular polarizing film, and an optical rotatory film.

* * * * *